US007220891B2

(12) United States Patent
Barsky et al.

(10) Patent No.: US 7,220,891 B2
(45) Date of Patent: May 22, 2007

(54) FELINE BRONCHIOLOALVEOLAR LUNG CARCINOMA XENOGRAFT AND CELL LINE

(75) Inventors: Sanford H Barsky, Los Angeles, CA (US); Deborah A. Grossman, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 442 days.

(21) Appl. No.: 10/477,501

(22) PCT Filed: May 28, 2002

(86) PCT No.: PCT/US02/16953

§ 371 (c)(1),
(2), (4) Date: Nov. 12, 2003

(87) PCT Pub. No.: WO02/096364

PCT Pub. Date: Dec. 5, 2002

(65) Prior Publication Data

US 2005/0118141 A1 Jun. 2, 2005

Related U.S. Application Data

(60) Provisional application No. 60/293,643, filed on May 25, 2001.

(51) Int. Cl.
*A01K 67/00* (2006.01)
*C12N 5/00* (2006.01)

(52) U.S. Cl. .......................... 800/9; 435/325; 435/326; 435/351; 800/8; 800/9; 800/10

(58) Field of Classification Search ..................... None
See application file for complete search history.

(56) References Cited

U.S. PATENT DOCUMENTS 5,939,455 A 8/1999 Rephaeli

FOREIGN PATENT DOCUMENTS

WO WO 94/06283 3/1994

OTHER PUBLICATIONS

Coll et al, Hum Gene Ther 1998;9:2063-74.*
York et al, J Virol 1992;66:4930-9.*
Hibi et al, Cancer Res 1998;58:5690-4.*
Gazdar et al, Cancer Res 1990;50:5481-7.*
Hahn et al, J Am Vet Med Assoc. 1997;211:1257-60.*
Sequence search print out, 2006, 3 pages.*
Bai, J., et al., "Unique Long Terminal Repeat U3 Sequences Distinguish Exogenous Jaagsiekte Sheep Retroviruses Associated with Ovine Pulmonary Carcinoma from Endogenous Loci in the Sheep Genome" J. of Virology, May 1996, vol. 70, No. 5, pp. 3159-3168.
Barksy, S., et al., "Rising Incidence of Bronchioloalveolar Lung Carcinoma and Its Unique Clinicopathologic Features" Cancer, Feb. 15, 1994, vol. 73, No. 4, pp. 1163-1170.
Barsky, S., et al., "The Multifocality of Bronchioloalveolar Lung Carcinoma: Evidence and Implications of a Multiclonal Origin" Modern Pathology, 1994, vol. 7, No. 6, pp. 633-640.
Barsky, S., et al., "The Extracellular Matrix of Pulmonary Scar Carcinomas Is Suggestive of a Desmoplastic Origin" American J. of Pathology, 1986, vol. 124, No. 3, pp. 412-419.
DeMartini, J., et al., "Jaagsiekte Sheep Retrovirus Proviral Clone $JSRV_{JS7}$, Derived from the JS7 Lung Tumor Cell Line, Induces Ovine Pulmonary Carcinoma and Is Integrated into the Surfactant Protein A Gene" J. of Virology, May 2001, vol. 75, No. 9, pp. 4239-4246.
Kitamura, H., et al., "Methods in Laboratory Investigation Long-Term Maintenance of Human Distal Airway Epithelial Cells in Nude Mice: A Potentially Useful Model for the Study of Pulmonary Carcinogenesis and Lung Cell Biology" Laboratory Investigation, Mar. 1990, vol. 62, No. 3, pp. 383-389.
Korsgaard, R., et al., "Propagation of a Poorly Differentiated Human Pulmonary Adenocarcinoma in Nude Athymic Rats" Int. J. of Cancer, Dec. 1983, vol. 32, No. 6, pp. 293-799.
Palmarini, M., et al., "Epithelial tumour cells in the lungs of sheep with pulmonary adenomatosis are major sites of replication for Jaagsiekte retrovirus" J. of General Virology, 1995, (76), pp. 2731-2737.
Palmarini, M., et al., "The Exogenous Form of Jaagsiekte Retrovirus Is Specifically Associated with a Contagious Lung Cancer of Sheep" J. of Virology, Mar. 1996, vol. 70, No. 3, pp. 1618-1623.
Palmarini, M., et al., "Jaagsiekte retrovirus establishes a disseminated infection of the lymphoid tissues of sheep affected by pulmonary adenomatosis" J of General Virology, 1996, (77), pp. 2991-2998.
Travis, W., et al., "Pulmonary Nodules Resembling Bronchioloalveolar Carcinoma in Adolescent Cancer Patients" Modern Pathology, Sep. 1998, vol. 1, No. 5, pp. 372-377.

* cited by examiner

*Primary Examiner*—Q. Janice Li
(74) *Attorney, Agent, or Firm*—Gates & Cooper LLP

(57) ABSTRACT

The present invention provides feline transplantable lung carcinoma xenografts and cell lines. Such xenografts and cell lines exhibit a number of unique characteristics which allows their use in experimental models of carcinoma in order to dissect out the molecular basis of this phenotype. This experimental model of carcinoma can be used to identify molecular targets for therapeutic intervention and to assess the efficacy of a broad spectrum of diagnostic and therapeutic agents. Specific animal models of lung cancer are described as well as methods for evaluating diagnostic and therapeutic agents for treating lung cancer.

9 Claims, 8 Drawing Sheets

FIG. 2
Karyotype of Feline BAC Cell Line
A1
A2
A3
B1
B2
B3
B4
C1
C2
D1
D1
D2
D3
E1
E2
E3
F1
F2
X
Y
Marker Chromosomes:

```
                1598
EXO SPA      GCTGCTTTGAGACCTTATCGAAAAAAGGGAGATCTATCTGATTTTATTCGCATTTGTGC
ENDO SPA     GCTGCTTTGAGACCTTATCGAAAGAAGGGAGATCTGTCTGACTTTATTCGCATTTGTGC
FELINE BAC   GCTGCTTTGAGACCTTATCGAAAAAAGGGAGATCTATCTGATTTTATTCGTATTTGTGC

                                   1700
TGATATTGGACCCTCCTACATGCAAGGCATTGCTATGGCAGCAGCATTACAAGGAAAAAGCATAAAAGAAGTACT
TGACATTGGGCCCTCCTATATGCAAGGTATTGCTATGGCGGCAGCATTACAAGGAAAAAGCATAAAGCAGGTACT
TGATATTGGGCCCTCTTATATGCAAGGTATTGCTATGGCGGCGGCATTACAGGGAAAAAGCATAAAAGAAGTACT

                                                                   1800
TTTCCAGCAGCAAGCCCGGAACAAGAAAGGACTTCAAAAGTCAGGTAATTCGGGTTGCTTTGTTTGTGGTCAGCC
TTTTCAGCAGCAAGCCCGGAACAAGAAAGGACTTCAAAAGTCAGGTAATTTGGGTTGCTTTGTTTGTGGTCAACC
TTTCCAACAACAAGCTCGAAATAAAAAAGGGCTTCAAAAATCAGGTAATTCAGGTTGCTTTGTCTGTGGTCAACC

                                  1826
TGGCCATCGGGCTGCAGTAT
TGGCCATCGAGCTGCAGTAT
TGGCCATCGGGCTGCAGTAT
```

FIG. 3A 1 2 3 4 bp 1598-1600 1649-51

JSRV Ala-*Ala*-Leu-Arg-Pro-Tyr-Arg-Lys-Lys-*Gly*-Asp-Leu-Ser-*Asp*-Phe-Ile-*Asp*-Ile-

F-BAC-Ala- -Gly- -Asp- -Asp- 1652-4 1709-11

-Cys-Ala-Asp-Ile-Gly-Pro-Ser-Tyr-Met-Gln-Gly-Ile-Ala-Met-Ala-Ala-Ala-Leu-Gln-Gly 5 1765-68

-Lys-Ser-Ile-Lys-*Glu*-Val-Leu-Phe-Gln-Gln-Gln-Ala-Arg-Asn-Lys-Lys-Gly-Leu-Gln-

F-BAC -*Glu*-

1769-71 1823-5

-Lys-Ser-Gly-Asn-Ser-Gly-Cys-Phe-Val-Cys-Gly-Gln-Pro-Gly-His-Arg-Ala-Ala-Val

FIG. 3B

| | 1598 |
|---|---|
| *EXO* SPA | GCTGCTTTGAGACCTTATCGAAAAAAGGGAGATCTATCTGATTTTATTCGCATTTGTGC |
| *ENDO* SPA | GCTGCTTTGAGACCTTATCGAAAGAAGGGAGATCTGTCTGACTTTATTCGCATTTGTGC |
| HUMAN BAC 1 | GCTGCTTTGAGACCTTATCGAAAAAAGGTAGTTCTGTCTGATTTTATTCGCATTTGTGC |
| HUMAN BAC 2 | GCTGCTTTGAGACCTTATCGAAAAAAGGGAGATCTGTCTGATTTTATTCGCATTTGTGC |
| HUMAN BAC 3 | GCTGCTTTGAGACCTTATCGAAAAAAGGGAGATTTATCTGATTTTATTCGCATTTGCGC |
| HUMAN BAC 4 | GCTGTTTTGAGACCTTATCGAAAAAAAGGAGTTCTATCTGTCTTTATTCGCATTTGTGC |
| HUMAN BAC 5 | GCTGCTTTGAGACCTTATCGAAAAAAGGGAGATCTATCTGATTTTATTCGCATTTGTGC |
| FELINE BAC | GCTGCTTTGAGACCTTATCGAAAAAAGGGAGATCTATCTGATTTTATTCGTATTTGTGC |

1700

TGATATTGGACCCTCCTACATGCAAGGCATTGCTATGGCAGCAGCATTACAAGGAAAAAGCATAAAAGA*__AGTACT__*
TGACATTGGGCCCTCCTATATGCAAGGTATTGCTATGGCGGCAGCATTACAAGGAAAAAGCATAAAGCA*__GGTACT__*
TGATATTGGACCCTCCTACATGCAAGGCATTGCTATGGCAGCAGCATTACAAGGAAAAAGCATAAAAGA*__GGTACT__*
TGACATTGGACCCTCCTACATGCAAGGCATTGCTATGGCAGCAGCATTACAAGGAAAAAGCATAAAAGA*__GGTACT__*
TGACATTGGACCCTCCTACATGCAAGGCATTGCTATGGCAGCAGCATTACAAGGAAAAAGCATAAAAGA*__GGTACT__*
TGACATTGGACCCTCCTACATGCAAGGCATTGCTATGGCAGCAGCATTACAAGGAAAAAGCATAAAAGA*__GGTACT__*
TGATATTGGACCCTCCTACATGCAAGGCATTGCTATGGCAGCAGCATTACAAGGAAAAAGCATAAAAGA*__AGTACT__*
TGATATTGGGCCCTCTTATATGCAAGGTATTGCTATGGCGGCGGCATTACAGGGAAAAAGCATAAAAGA*__AGTACT__*

1800

TTTCCAGCAGCAAGCCCGGAACAAGAAAGGACTTCAAAAGTCAGGTAATTCGGGTTGCTTTGTTTGTGGTCAGCC
TTTTCAGCAGCAAGCCCGGAACAAGAAAGGACTTCAAAAGTCAGGTAATTTGGGTTGCTTTGTTTGTGGTCAACC
TTTCCAGCAGCAAGCCCGGAACAAGAAAGGACTTCAAAAGTCAGGTAATTCGGGTTGCTTTGTTTGTGGTCAGCC
TTTCCAGCAGCAAGCCCGGAACAAGAAAGGACTTCAAAAGTCAGGTAATTTGGGTTGCTTTGTTTGTGGTCAGCC
TTTTCAGCAGCAAGCCCGGAACAAGAAAGGACTTCAAAAGTCAGGTAATTCGGGTTGCTTTGTTTGTGGTCAACC
TTTCCAGCAGCAAGCCCGGAACAAGAAAGGACTTCAAAAGTCAGGTAATTCGGGTTGCTTTGTTTGTGGTCAGCC
TTTCCAGCAGCAAGCCCGGAACAAGAAAGGACTTCAAAAGTCAGGTAATTCGGGTTGCTTTGTTTGTGGTCAGCC
TTTCCAACAACAAGCTCGAAATAAAAAAGGGCTTCAAAAATCAGGTAATTCAGGTTGCTTTGTCTGTGGTCAACC

1826

TGGCCATCGGGCTGCAGTAT
TGGCCATCGAGCTGCAGTAT
CGGCCATCGAGCTGCAGTAT
TGGCCATCGGGCTGCAGTAT
TGGCCATCGGGCTGCAGTAT
CGGCCATCGAGCTGCAGTAT
TGGCCATCGGGCTGCAGTAT
TGGCCATCGGGCTGCAGTAT

FIG. 4A

| | 1 | | 2 | | 3 | | 4 | |
|---|---|---|---|---|---|---|---|---|
| bp 1598-1600 | | | | | | | | 1649-51 |
| JSRV | Ala-*Ala*- | Leu-Arg-Pro-Tyr-Arg-Lys-Lys- | *Gly*- | Asp-Leu-Ser- | *Asp*- | Phe-Ile- | *Asp*- | Ile- |
| BAC 1 | -Ala- | | -Val- | | -Val- | | -Asp- | |
| BAC 2 | -Ala- | | -Gly- | | -Val- | | -Asp- | |
| BAC 3 | -Ala- | | -Gly- | | -Asp- | | -Asp- | |
| BAC 4 | -Val- | | -Gly- | | -Asp- | | -Val- | |
| BAC 5 | -Ala- | | -Gly- | | -Asp- | | -Asp- | |
| F-BAC | -Ala- | | -Gly- | | -Asp- | | -Asp- | |

1652-4 1709-11

-Cys-Ala-Asp-Ile-Gly-Pro-Ser-Tyr-Met-Gln-Gly-Ile-Ala-Met-Ala-Ala-Ala-Leu-Gln-Gly

| | 5 | | 1765-68 |
|---|---|---|---|
| -Lys-Ser-Ile-Lys- | <u>*Glu*</u>- | Val-Leu-Phe-Gln-Gln-Gln-Ala-Arg-Asn-Lys-Lys-Gly-Leu-Gln- | |
| BAC 1 | -Gln- | | |
| BAC 2 | -Gln- | | |
| BAC 3 | -Gln- | | |
| BAC 4 | -Gln- | | |
| BAC 5 | -<u>*Glu*</u>- | | |
| F-BAC | -<u>*Glu*</u>- | | |

1769-71 1823-5

-Lys-Ser-Gly-Asn-Ser-Gly-Cys-Phe-Val-Cys-Gly-Gln-Pro-Gly-His-Arg-Ala-Ala-Val

FIG. 4B

SEQUENCE LISTING

```
<160> NUMBER OF SEQ ID NOS: 19

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1

gctgctttra gaccttatcg aaa                                    23


<210> SEQ ID NO 2
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (0)...(0)
<223> OTHER INFORMATION: y = c or t

<400> SEQUENCE: 2

atactgcagc ycgatggcca g                                      21
```

-continued

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggcgcctatg gtttccattt ag 22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
catccagtgg cttcttcttt tg 22

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gactgaatat aaacttgtgg 20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctataatggt gaatatcttc 20

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gacggaatat aagctggt 18

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
cctgtactgg tggatgtcc 19

<210> SEQ ID NO 9
<211> LENGTH: 20
<212> TYPE: DNA
<213> ORGANISM: Artificial Sequence
<220> FEATURE:
<223> OTHER INFORMATION: Primer -continued

<400> SEQUENCE: 9
gactgagtac aaactggtgg 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ctgtagaggt taatatccgc 20

<210> SEQ ID NO 11
<211> LENGTH: 229
<212> TYPE: DNA
<213> ORGANISM: Jaagsiekte virus

<400> SEQUENCE: 11
gctgctttga gaccttatcg aaaaaaggga gatctatctg attttattcg catttgtgct 60
gatattggac cctcctacat gcaaggcatt gctatggcag cagcattaca aggaaaaagc 120
ataaaagaag tacttttcca gcagcaagcc cggaacaaga aaggacttca aaagtcaggt 180
aattcgggtt gctttgtttg tggtcagcct ggccatcggg ctgcagtat 229

<210> SEQ ID NO 12
<211> LENGTH: 229
<212> TYPE: DNA
<213> ORGANISM: Jaagsiekte virus

<400> SEQUENCE: 12
gctgctttga gaccttatcg aaagaaggga gatctgtctg actttattcg catttgtgct 60
gacattgggc cctcctatat gcaaggtatt gctatggcgg cagcattaca aggaaaaagc 120
ataaagcagg tactttttca gcagcaagcc cggaacaaga aaggacttca aaagtcaggt 180
aatttgggtt gctttgtttg tggtcaacct ggccatcgag ctgcagtat 229

<210> SEQ ID NO 13
<211> LENGTH: 229
<212> TYPE: DNA
<213> ORGANISM: Felis domesticus

<400> SEQUENCE: 13
gctgctttga gaccttatcg aaaaaaggga gatctatctg attttattcg tatttgtgct 60
gatattgggc cctcttatat gcaaggtatt gctatggcgg cggcattaca gggaaaaagc 120
ataaaagaag tacttttcca acaacaagct cgaaataaaa aagggcttca aaaatcaggt 180
aattcaggtt gctttgtctg tggtcaacct ggccatcggg ctgcagtat 229

<210> SEQ ID NO 14
<211> LENGTH: 229
<212> TYPE: DNA
<213> ORGANISM: Homo Sapiens

<400> SEQUENCE: 14
gctgctttga gaccttatcg aaaaaaggta gttctgtctg attttattcg catttgtgct 60
gatattggac cctcctacat gcaaggcatt gctatggcag cagcattaca aggaaaaagc 120
ataaaagagg tacttttcca gcagcaagcc cggaacaaga aaggacttca aaagtcaggt 180

-continued

```
aattcgggtt gctttgtttg tggtcagccc ggccatcgag ctgcagtat              229


<210> SEQ ID NO 15
<211> LENGTH: 229
<212> TYPE: DNA
<213> ORGANISM: Homo Sapiens

<400> SEQUENCE: 15

gctgctttga gaccttatcg aaaaaaggga gatctgtctg attttattcg catttgtgct     60

gacattggac cctcctacat gcaaggcatt gctatggcag cagcattaca aggaaaaagc    120

ataaaagagg tacttttcca gcagcaagcc cggaacaaga aaggacttca aaagtcaggt    180

aatttgggtt gctttgtttg tggtcagcct ggccatcggg ctgcagtat              229


<210> SEQ ID NO 16
<211> LENGTH: 229
<212> TYPE: DNA
<213> ORGANISM: Homo Sapiens

<400> SEQUENCE: 16

gctgctttga gaccttatcg aaaaaaggga gatttatctg attttattcg catttgcgct     60

gacattggac cctcctacat gcaaggcatt gctatggcag cagcattaca aggaaaaagc    120

ataaaagagg tactttttca gcagcaagcc cggaacaaga aaggacttca aaagtcaggt    180

aattcgggtt gctttgtttg tggtcaacct ggccatcggg ctgcagtat              229


<210> SEQ ID NO 17
<211> LENGTH: 229
<212> TYPE: DNA
<213> ORGANISM: Homo Sapiens

<400> SEQUENCE: 17

gctgttttga gaccttatcg aaaaaaagga gttctatctg tctttattcg catttgtgct     60

gacattggac cctcctacat gcaaggcatt gctatggcag cagcattaca aggaaaaagc    120

ataaaagagg tacttttcca gcagcaagcc cggaacaaga aaggacttca aaagtcaggt    180

aattcgggtt gctttgtttg tggtcagccc ggccatcgag ctgcagtat              229


<210> SEQ ID NO 18
<211> LENGTH: 229
<212> TYPE: DNA
<213> ORGANISM: Homo Sapiens

<400> SEQUENCE: 18

gctgctttga gaccttatcg aaaaaaggga gatctatctg attttattcg catttgtgct     60

gatattggac cctcctacat gcaaggcatt gctatggcag cagcattaca aggaaaaagc    120

ataaaagaag tacttttcca gcagcaagcc cggaacaaga aaggacttca aaagtcaggt    180

aattcgggtt gctttgtttg tggtcagcct ggccatcggg ctgcagtat              229


<210> SEQ ID NO 19
<211> LENGTH: 76
<212> TYPE: PRT
<213> ORGANISM: Jaagsiekte

<400> SEQUENCE: 19

Ala Ala Leu Arg Pro Tyr Arg Lys Lys Gly Asp Leu Ser Asp Phe Ile
 1               5                  10                  15

Asp Ile Cys Ala Asp Ile Gly Pro Ser Tyr Met Gln Gly Ile Ala Met
            20                  25                  30
```

-continued

```
Ala Ala Ala Leu Gln Gly Lys Ser Ile Lys Glu Val Leu Phe Gln Gln
        35                  40                  45

Gln Ala Arg Asn Lys Lys Gly Leu Gln Lys Ser Gly Asn Ser Gly Cys
    50                  55                  60

Phe Val Cys Gly Gln Pro Gly His Arg Ala Ala Val
65                  70                  75
```

FELINE BRONCHIOLOALVEOLAR LUNG CARCINOMA XENOGRAFT AND CELL LINE

RELATED APPLICATIONS

This application claims priority under Section 119(e) from U.S. Provisional Application Ser. No. 60/293,643 filed May 25, 2001, the contents of which are incorporated herein by reference.

FIELD OF THE INVENTION

The present invention relates to the use of feline lung carcinoma xenografts and cell lines as models for both the evaluation of the cancer phenotype as well as the generation of novel diagnostic and therapeutic methods for the clinical management of this pathology.

BACKGROUND OF THE INVENTION

Over the past decade, there has been a marked increase in both the number of new cases and in deaths related to lung cancer nationwide. Tobacco (cigarette smoking) has been implicated in the initiation and promotion of the majority of these new cases of lung cancer. Carcinogens and tumor promoters in cigarette smoke are thought to be responsible for many of the genetic and epigenetic alterations in bronchial and alveolar epithelial cells that result in the multistep progression into lung cancer.

Peripheral adenocarcinoma (PAC) and bronchioloalveolar carcinoma (BAC) are forms of lung cancer whose etiology and pathogenesis are controversial and whose link to either main stream tobacco smoking or second hand smoking unproven. While squamous cell carcinomas and small cell carcinomas have shown an overall decrease in incidence in the past decade, peripheral adenocarcinomas (PACs) and bronchioloalveolar lung cancers (BACs) have shown an exponential increase (Barsky et al., Cancer 1994; 73: 1163–1170; Barsky et al., Modern Path 1994; 7: 633–640). These increases have been observed equally in both smokers as well as non-smokers. These epidemiological observations provide evidence that either different etiological factors exist (other than main stream or second hand smoke) that cause PACs and BACs or that different etiological co-factors that are synergistic with main stream or second hand smoke play a role in the genesis of PAC/BAC. Some of the distinguishing pathological, biological epidemiological and perhaps etiological features which distinguish PAC/BAC from other types of lung cancer are its peripheral location, its association with desmoplasia (scarring) (Barsky et al., Am J Pathol 1986; 124:412–419), its significant occurrence in non-smokers, its comparatively high female/male ratio, and its tendency to appear in multiple and bilateral foci (especially BAC). Although some theories suggest that this multifocality is due to intrapulmonary metastatic spread or a combination of aerosolization and aspiration, we have demonstrated that at least a partial basis for this multifocality or multicentricity is multiclonality (Barsky et al., Cancer 1994; 73: 1163–1170; Barsky et al., Modern Path 1994; 7: 633–640).

The multifocal nature of BAC was first described in 1876 Malassez et al., Archives of Physiology and Normal Pathology 1876; 3:353–372). BAC was further defined as a well-differentiated adenocarcinoma occurring in the periphery of the lung which tended to spread along aerogenous and lymphatic routes within the confines of the lung (Liebow, Bronchiolar-alveolar carcinoma. Adv Intern Med 1960;

10:329–358). In the revised WHO lung tumor classification (ICD-0) (World Health Organization. Histological typing of lung tumors. International histological classification of tumors, 2nd ed. Geneva. WHO. 1981), bronchioloalveolar carcinoma was included as a subtype of adenocarcinoma. Although there has been considerable debate as to whether bronchioloalveolar carcinoma represents a distinct clinical entity separate from other adenocarcinomas (Schraufnagel et al., Am Rev Resp Dis 1982; 125:74–79), recent evidence suggests differences in incidence trends, survival, and sex and age distributions compared to other adenocarcinomas and other lung cancer cell types (Grover et al., Ann Surg 1989; 209:779–90). For these reasons BAC should be considered as a distinct clinicopathological entity. Pathologists categorize BAC into mucinous and non-mucinous on the basis of their microscopic appearance and further subcategorize non-mucinous BAC into Clara, Type II pneumocyte and mixed cell of origin on the basis of ultrastructural and immunocytochemical findings (Yoneda K Cancer 1990; 164–169).

Peripheral adenocarcinoma has long been the predominant cell type among female lung cancers (Wynder et al., Eur J Clin Oncol 1987; 23:1491–1496) and there is abundant evidence that this cell type has been increasing in both men and women (Vincent et al., Cancer 1977; 39:1647–1655; Dodds et al., JNCI 1986; 76:21–29; Valaitis et al., Cancer 1981;47:1042–1046; Percy et al., Lung cancer: causes and prevention. Mizell M, Correa P, eds. Verlag Chemie International Inc. 1984). According to SEER data for 1973–1981 (Percy et al., Lung cancer: causes and prevention. Mizell M, Correa P, eds. Verlag Chemie International Inc. 1984), the incidence of adenocarcinoma has increased 3% per year in males compared to 1.50% per year in females. In 1981, 25% of white male lung cancers and 35% of white female lung cancers were adenocarcinoma. Increases in the proportion of adenocarcinomas have also been reported in Japan (Tsugane et al., Jpn J Can Res 1987; 78:162–169; Watanabe et al., Jpn J Cancer Res 1987; 78:460–6) and Israel (Rennert et al., Cancer Det Prev 1991; 15:99–101). Few studies report the proportion of bronchioloalveolar carcinomas separately from other adenocarcinomas. In SEER data (Percy et al., Lung cancer: causes and prevention. Mizell M, Correa P, eds. Verlag Chemie International Inc. 1984), 17% of adenocarcinomas were bronchioloalveolar carcinomas, 15% were other subtypes, and 68% were classified adenocarcinoma NOS. While bronchioloalveolar carcinoma (BAC) represented approximately 3.5% of all lung cancers in the SEER data Percy et al., JNCI 1983; 70:663–666), other studies have reported this proportion to vary from 1% to 8% (Liebow ". Bronchiolar-alveolar carcinoma. Adv Intern Med 1960; 10:329–358; Thomas et al., Br J Dis Chest 1985; 79:132–140; Bennett et al., Cancer 1969; 24:876–887). Recently, there have been several reports of an increase in the incidence of bronchioloalveolar carcinomas. Among patients included in seven Lung Cancer Study Group protocols between 1977 and 1988, 14.5% met the classification criteria for bronchioloalveolar carcinoma (Grover et al., Ann Surg 1989; 209:779–90). In a 1988 study (Gazdar et al.,. Sem Onc 1988; 15:215–225), the authors noted that bronchioloalveolar carcinoma was being diagnosed with increasing frequency in the Washington-Baltimore area. In a study of 505 autopsied cases of lung cancer diagnosed between 1973 and 1989 in New Jersey, other authors (Auerbach et al., Cancer 1991; 68:1973–1977) found that the incidence of bronchioloalveolar carcinoma increased from 9.3% to 20.3%, more than any other cell type. A similar increase was reported in Japan (Ikeda et al., Lung cancer 1991;

7:157164). For the time period 1982–1985, 71% of all adenocarcinomas were classif as a the bronchioloalveolar subtype. It is not clear how much, if any, of the recent increases observed for BAC can be explained by changes in diagnostic criteria.

While lung cancer typically shows a strong male predominance, the male/female ratio varies with histologic type. The male/female incidence ratios vary from a high for squamous cell carcinoma (M/F=2.4) to a low for adenocarcinoma (M/F=1.4) (Anton-Culver et al., Cancer Res 1988; 48:6580–6583). The male/female ratio for bronchioloalveolar carcinoma has been reported to range from that observed in all adenocarcinomas to less than unity. Two studies (Bennett et al., Cancer 1969; 24:876–887; Ikeda et al., Lung cancer 1991; 7:157164) reported a lesser male predominance for bronchioloalveolar carcinoma compared to all lung cancers but similar to that for all adenocarcinomas. Among patients included in the Lung Cancer Study Group protocols, a male/female ratio of 1.4 was observed for bronchioloalveolar carcinoma compared to 1.7 for other adenocarcinomas (Grover et al., Ann Surg 1989; 209:779–90). Similarly, the male predominance among SEER cases was less for bronchioloalveolar carcinoma (1.2) than for other adenocarcinomas (1.8) (Percy et al., Lung cancer: causes and prevention. Mizell M, Correa P, eds. Verlag Chemie International Inc. 1984). Another study (Schraufnagel et al., Am Rev Resp Dis 1982; 125:7479) however, reported an excess of bronchioloalveolar carcinoma in females compared to males. The male predominance for bronchioloalveolar carcinoma is clearly less than for other types of lung cancer and evidence suggests that it is close to, and possibly less than, unity. Studies of lung cancer cell types consistently report a younger age at diagnosis for adenocarcinoma (including bronchioloalveolar carcinoma) than for other cell types in both men and women (Anton-Culver et al., Cancer Res 1988; 48:6580–6583; McDuffie et al., J Clin Epidmiol 1991; 44:537–544; Greenberg et al., JNCI 1984; 72:599–603; Tsai et al., Cancer Det Prev 1988; 11:235–238). Few studies have compared the age distribution for cases of bronchioloalveolar carcinoma alone with other cell types. Two studies (Liebow, Bronchiolar-alveolar carcinoma. Adv Intern Med 1960; 10:329–358; Storey et al., J Thorac Surg 1953; 26:331–403) described bronchioloalveolar carcinoma as occurring with higher frequency in younger ages compared to other cell types. Another study (Schraufnagel et al., Am Rev Resp Dis 1982; 125:74–79) noted the same age distribution for bronchioloalveolar carcinoma and other adenocarcinomas but younger than for squamous cell carcinomas. Contrary to these reports, the Lung Cancer Study Group (Grover et al., Ann Surg 1989; 209:779–90) reported that bronchioloalveolar carcinoma occurs more frequently in older patients than does adenocarcinoma. It is not clear at this time whether or not the age distribution for bronchioloalveolar carcinoma differs from other adenocarcinomas. Survival for bronchioloalveolar carcinoma compared favorably with other adenocarcinomas and large cell carcinoma in the Lung Cancer Study Group experience (Grover et al., Ann Surg 1989; 209:779–90). Survival rates during the first two years after diagnosis were also better than for squamous cell carcinoma, although survival rates were equal after two years.

Adenocarcinoma of the lung has been shown to be associated with cigarette smoking but not as strongly associated with smoking as squamous or small cell carcinomas (McDuffie et al., Cancer 1987; 59:1825–30; Anton-Culver et al., Cancer Res 1988; 48:6580–6583; Osann et al., Cancer Res 1991; 51:4893–4897; Schoenberg et al., Am J Epidemiol 1989; 130:688–695). Risk ratios for adenocarcinoma associated with cigarette smoking in New Jersey men and women were 4.8 and 3.6 respectively (Schoenberg et al., Am J Epidemiol 1989; 130:688–695). Relative risks have not been calculated for bronchioloalveolar carcinoma. One study (Ikeda et al., Lung cancer 1991; 7:157164) noted a similar rate of tobacco use among cases of bronchioloalveolar carcinoma as for the overall group of adenocarcinomas. Others reported a higher proportion of non-smokers among cases of bronchioloalveolar carcinoma than among other adenocarcinomas (Schraufnagel et al., Am Rev Resp Dis 1982; 125:74–79; Auerbach et al., Cancer 1991; 68:1973–1977) and lower mean pack-years of exposure to cigarettes compared to other cell types (Schraufnagel et al., Am Rev Resp Dis 1982; 125:7479). The Lung Cancer Study Group (Grover et al., Ann Surg 1989; 209:779–90) reported that patients with bronchioloalveolar carcinoma were significantly less likely to have a history of smoking than were other cases of adenocarcinoma. While it is clear that bronchioloalveolar carcinoma is at most weakly associated with smoking, it is not clear whether the association with smoking differs from that observed for other adenocarcinomas. Because the association with smoking is weak at best, smoking is an unlikely explanation for the recent increases observed.

Exposure to sidestream or secondhand smoke in the home and workplace have been shown to double the risk of lung cancer in non-smokers (Janerich et al., New Engl J Med 1990; 323:632–6). Passive smoking significantly increased risk for adenocarcinoma in a study of Chinese women (Lam et al., Br J Cancer 1987; 55:673–8). However, no significant increase in risk for adenocarcinoma with passive smoking was noted in another study (Wu et al., JNCI 1985; 74:747–751). An increase in lung cancer risk associated with exposure to cooking oil vapors has also been reported (Gao et al., In J Cancer 1987; 40:604609). The importance of passive smoke for bronchioloalveolar carcinoma has not been well studied.

Incidence of bronchioloalveolar carcinoma is increased in patients with scleroderma (Montgomery R D, Stirling G A, Hamer N A J. Bronchiolar carcinoma in progressive systemic sclerosis. Lancet 1964; 1:586–7) and is associated with parenchymal scarring and interstitial inflammation of the lung (Liebow "Bronchiolar-alveolar carcinoma" Adv Intern Med 1960; 10:329–358; Marcq et al, Am Rev Respir Dis 1973; 107:621–629). Although 60% of bronchioloalveolar carcinomas in one study had radiographic evidence of a prior lesion in the same location as the tumor, no cases gave a medical history of illness including emphysema, tuberculosis, pneumonia, or pulmonary thromboembolism which could have caused scarring (Schraufnagel et al., Am Rev Resp Dis 1982; 125:74–79). Experimental evidence suggests that the scarring may be the result of the cancer rather than the cause (Barsky et al., Am J Pathol 1986; 124:412–419). The Lung Cancer Study Group reported that patients with bronchioloalveolar carcinoma were less likely than other adenocarcinoma patients to have a history of chronic lung disease (Grover et al., Ann Surg 1989; 209: 779–90). However, this variable was highly correlated with smoking. Contamination of indoor air by radon from soil, water, or building materials has been shown to be a potentially important cause of lung cancer (Samet J M., JNCI 1989; 81:745–757). Exposure to radon in homes appears to carry only a small increase in risk for non-smokers (Svensson et al., Cancer Res 1989; 49:1861–1865). When risks were estimated by histologic type, this study (Svensson et al., Cancer Res 1989; 49:1861–1865) also noted that adenocarcinoma had the lowest increase in risk associated with radon exposure in homes of any cell type. Small cell carcinoma has most frequently been reported as the predominant type of lung cancer in uranium miners exposed to radon (Samet J M., JNCI 1989; 81:745–757). Although there have been no reports of an increase in bronchioloalveolar lung cancer in uranium miners, contamination of indoor air could contribute to an excess of this cell type in women who are more likely to spend time at home. Occupational risk factors for bronchioloalveolar carcinoma have not been identified. One study (Schraufnagel et al., Am Rev Resp Dis 1982; 125:74–79) found no clear predominance of any occupational group in his series of bronchioloalveolar lung cancer cases. Squamous and small cell carcinomas have most frequently been associated with occupational exposures. However, an increase in the proportion of adenocarcinomas has been noted with exposure to asbestos, beryllium, and polyvinyl chloride (Ives et al., Am Rev Respir Dis 1983; 128:195–209). Because of the equal frequencies of this cancer in men and women, and because occupational exposures are more common in men than in women, it is unlikely that occupation is responsible for the recent increase in this disease.

Because cats and dogs get tumors that clinicopathologically resemble their human counterparts yet presumably are not exposed to the same types of exogenous carcinogenic factors, a study of their molecular alterations might be revealing. Bronchioloalveolar lung carcinoma (BAC) is an example of such a cancer which involves the lungs diffusely in all three species.

Unlike other forms of lung cancer, BAC naturally occurs in two non-human species: sheep and cats. Neither of these animals are exposed to main stream or second hand smoke. Human BAC closely resembles histologically an infectious endemic disease of sheep called jaagsiekte (Bonne et al., Am J Cancer 1939; 35:491–501; De la Heras et al., Eur Respir J. 2000 Aug.;16(2):330–2. The sheep form occurs as ovine pulmonary adenomatosis or jaagsiekte, a disease caused by an exogenous retrovirus (JSRV). In sheep, the disease manifests as a diffuse pulmonic adenomatosis commonly called SPA for short. The SPA complex is of particular interest, since: at least some, and probably all, forms are infectious; members of the SPA complex range in pathology from inflammatory or infiltrative to carcinomatous; and various forms of SPA, while almost certainly of viral etiology, can occur in both epizootic and enzootic form, thus resembling both the picture of classic viral transmission (epizootic) and that of natural tumor epidemiology (occurring at low rates, or enzootic) in which viruses are not ordinarily thought to be implicated. Retrovirus-induced pulmonary carcinoma in sheep was achieved experimentally about a decade ago (DeMartini et al., JNCI 1987; 79:167–177). The cell of origin that gives rise to sheep jaagsiekte is thought to be the Type II pneumocyte, a cell thought also to give origin to one subtype of human non-mucinous BAC. The exogenous virus thought responsible for jaagsiekte has been cloned and reliably distinguished from endogenous retroviral sequences (Palmarini et al., J of General Virology 1995: 76: 2731–2737; Palmarini et al., J of Virology 1996; 70: 1618–1623; Palmarini et al., J of Gen Virology 1996a; 77: 2991–2998; Bai et al., J of Virology 1996; 70: 3159–3168). The feline form naturally occurs in old (>10 years) pure bred Persian and Himalayan cats. The cat form of BAC has not been at all studied and is not endemic nor contagious. It occurs sporadically and spontaneously in older pure bred cats, especially Persian and Himalayan. With respect to its sporadic and spontaneous nature, it has more similarities to human BAC than does sheep BAC (jaagsiekte). Feline BAC is also thought to be of Type II pneumocyte origin.

As is known in the art, animals and humans are affected by a variety of related and/or common pathogens. For example cats are frequently infected with or are carriers of toxoplasmosis, an infectious organism which can seriously harm the developing human fetus in pregnant women. It has been difficult to grow toxoplasmosis in culture and develop a vaccine against this disease. But since cats are the natural host for this organism, it has been suggested that feline cells may provide a nurturing environment for growing organisms such as toxoplasmosis in vitro. Consequently, there is a need in the art for reagents such as mammalian cell lines that can be used in the examination of mammalian pathogens. In addition, there is a need in the art for reagents such as mammalian cell lines that can be used in the examination of mammalian cancers such as BAC. The invention disclosed herein meets these needs.

SUMMARY OF THE INVENTION

The invention disclosed herein provides a model system for studying human and related mammalian pathologies such as BAC. In particular, the present invention provides transplantable xenograft (SPARKY-X) and cell line (SPARKY) derived from a malignant pleural effusion of a 12 year-old Persian male with autopsy-confirmed BAC. SPARKY-X exhibits a classic lepidic BAC growth pattern and stimulated angiogenesis and stroma. SPARKY exhibits a type II pneumocyte origin: lamellar bodies ultrastructurally and surfactant expression by Northern blot. SPARKY's karyotype was aneuploid (66 chromosomes: 38=diploid). P53 showed a G to T transversion at codon 167, the feline equivalent of human codon 175, one of the many hot spots mutated in smokers. Ha-ras, Ki-ras were not altered. In addition, as shown by RT-PCR, SPARKY expresses retroviral gag transcripts which Ore 90% identical to exogenous JSRV (jaagsiekte retrovirus), the retroviral cause of sheep BAC. The feline transcripts of SPARKY, like the exogenous JSRV retroviral transcripts, contains a Sca I site. The molecular alterations observed in SPARKY that are shared with sheep and human lung cancers provides evidence of an overlapping pathway of tumorigenesis. The disclosure provided herein teaches methods in which SPARKY-X and SPARKY can be used in methods of evaluating pathogens such as jaagsiekte-type retroviruses and *Toxoplasma gondii* in vitro and in vivo.

As noted above, the inventions disclosed herein relate to feline transplantable lung xenografts and cell lines. These cells exhibit a number of unique characteristics which allows the skilled artisan to use them in experimental models of lung cancer in order to dissect out the molecular basis of this phenotype. Moreover, this experimental model of lung cancer can be used to identify molecular targets for therapeutic intervention and to assess the efficacy of a broad spectrum of diagnostic and therapeutic agents.

One embodiment of the invention consists of a feline lung cancer xenograft. In a preferred embodiment the xenograft is the feline xenograft referred to as SPARKY-X deposited with the American Type Culture Collection, 10801 University Boulevard, Manassas, Va., USA (ATCC) on Jan. 19, 2001 and received patent deposit designation PTA-2920. A related embodiment of the disclosed invention consists of an in vitro cell line culture deposited with the ATCC on Jan. 19, 2001 and received patent deposit designation PTA-2919.

Methods for generating the disclosed xenografts are also described. Another embodiment of the invention consists of methods of identifying a molecule whose expression is modulated in lung cancer by determining the level of expression of at least one molecule in the feline lung cancer xenograft; and comparing this to the level of expression of the same molecule in a cell having characteristics which are distinct from the feline lung cancer xenograft. In preferred embodiments of this invention, the level of expression of the molecule of the lung cancer xenograft is determined by methods selected from the group consisting of: Northern blotting, Southern blotting, Western blotting and polymerase chain reaction.

Yet another embodiment of the invention consists of an animal model for lung cancer comprising an immunocompromised host animal inoculated with a feline lung cancer xenograft. In preferred embodiments of this invention, the host animal is a nude mouse and the xenograft is the xenograft designated SPARKY-X. Another embodiment of the invention consists of methods for evaluating at least one agent for treating lung cancer by utilizing a immunocompromised host animal inoculated with a feline lung cancer xenograft, administering at least one agent to said inoculated immunocompromised host animal and evaluating the effects of the agent(s) on the feline lung cancer xenograft. Optionally, the agent that is being evaluated targets a molecule that is identified as being associated with the oncogenic phenotype.

Another embodiment of the invention comprises a method of culturing a pathogen in the disclosed feline cells by inoculating the cell line with the pathogen and growing the pathogen under conditions known to facilitate its growth. Optionally the pathogen is toxoplasmosis gondii and is cultured and recovered by methods known in the art.

BRIEF DESCRIPTION OF THE DRAWINGS

FIG. 3A: Results of JSRV gag sequencing in feline BAC showing the homology between JSRV gag sequences in Jaagsiekte and feline BAC. A comparison of feline BAC to exogenous shows the presence of a Sca I site and 19 mismatched (91.7% homology). A comparison of feline BAC to endogenous shows the presence of a Sca I site and 24 mismatched (89.5% homology). The nucleotide sequences in this figure include EXO SPA (SEQ ID NO: 11), ENDO SPA (SEQ ID NO: 12), and feline BAC (SEQ ID NO: 13).

FIG. 3B: Results of amino add comparison in feline BAC showing the amino add fidelity of JSRV gag transcripts (SEQ ID NO: 19) in Jaagsiekte and feline BAC (F-BAC).

FIG. 4A: Results of JSRV gag sequencing in human BAC showing homology between jsrv gag sequences in a jaagsiekte and five cases of human BAC/PAC and one case of feline BAC. The nucleotide sequences in this figure include EXO SPA (SEQ ID NO: 11), ENDO SPA (SEQ ID NO: 12), feline BAC (SEQ ID NO: 13), and human BAC 1–human BAC 5 (SEQ ID Nos: 15–18 respectively).

FIG. 4B: Results of amino acid comparison in human BAC showing the amino acid fidelity of JSRV gag transcripts (SEQ ID NO: 19 in jaagsiekte, human BAC/PAC and feline BAC.

DETAILED DESCRIPTION OF THE INVENTION

Figure 1A:
FIG. 1A: Low power magnification of photomicrograph of Spark's lung shows bronchioloalveolar pattern, so-called lepidic pattern of BAC.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/ox for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in see Ausubel et al., Current Protocols in Molecular Biology, Wiley Interscience Publishers, (1995) and Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Embodiments of the invention disclosed herein relate to feline lung carcinoma xenografts (SPARKY-X) and cell lines (SPARKY). The cells, animal models and assays disclosed herein allow one to analyze the cellular and molecular mechanisms associated with the oncogenesis of cells of the bronchioloalveolar lineage, which will lead to better methodological tools for diagnosing and treating diseases such as lung cancers. For example, as described in detail below, SPARKY and SPARKY-X exhibit a number of unique characteristics which allows the skilled artisan to use them in experimental models of lung carcinoma to, for example, dissect out the molecular basis of this phenotype. Moreover, these experimental models of lung carcinoma can be used to identify molecular targets for therapeutic intervention and to assess the efficacy of a broad spectrum of diagnostic and therapeutic agents. The invention further provides methods of culturing pathogens in the disclosed feline cells by inoculating the cells with the pathogen and growing the pathogen under conditions known to facilitate its growth. Optionally the pathogen so cultured can be recovered by methods known in the art. Certain methods and reagents of the invention are related to PCT International Application No. PCT/US00/25299, published on Mar. 22, 2001 under International Publication No. WO 01/19967, which is incorporated herein by reference.

Establishing Feline BAC Xenografts and BAC Cell Lines

A 12 year old Persian cat, named Sparky presented with shortness of breath and was found to have bilateral pleural effusions which contained malignant cells on pleuracentesis. These cells were cultured and gave rise to an immortal cell line, SPARKY. In general the vast majority of successfully established human and animal cell lines have been obtained from pleural effusions as was the case with SPARKY.

Without being bound by specific theory, this is believed to be influenced by two things: the fact that contaminating fibroblasts are not present in pleural effusions and are not able therefore to overgrow the culture and the fact that malignant cells in pleural effusions have already "adapted" to growing in a culture media of sorts. The successful establishment of such a cell line (SPARKY) and subsequent xenograft (SPARKY-X) provides novel models that allow for the study of common animal-human pathogens implicated in cancer and infectious disease. Embodiments of the invention that relate to establishing the feline BAC xenografts consist of obtaining cells from a pleural effusion via methods known in the art (e.g. biopsy) and transplanting them (preferably subcutaneously) in to an non-feline immunocompromised host, allowing the cells to proliferate and then isolating feline cells from the host. Optionally the cells are passaged in the host serially prior to their isolation and characterization. Embodiments of the invention that relate to establishing the feline BAC xenografts consist of obtaining cells from a pleural effusion via methods known in the art (e.g. needle biopsy) and placing them in tissue culture under conditions amenable to their growth, allowing them to proliferate and then isolating the cells. Optionally the cells are passaged in the culture serially (e.g. serial dilution to establish clonal populations) prior to their isolation and characterization.

Characterizing Feline BAC Xenografts and BAC Cell Lines

Figure 1B:
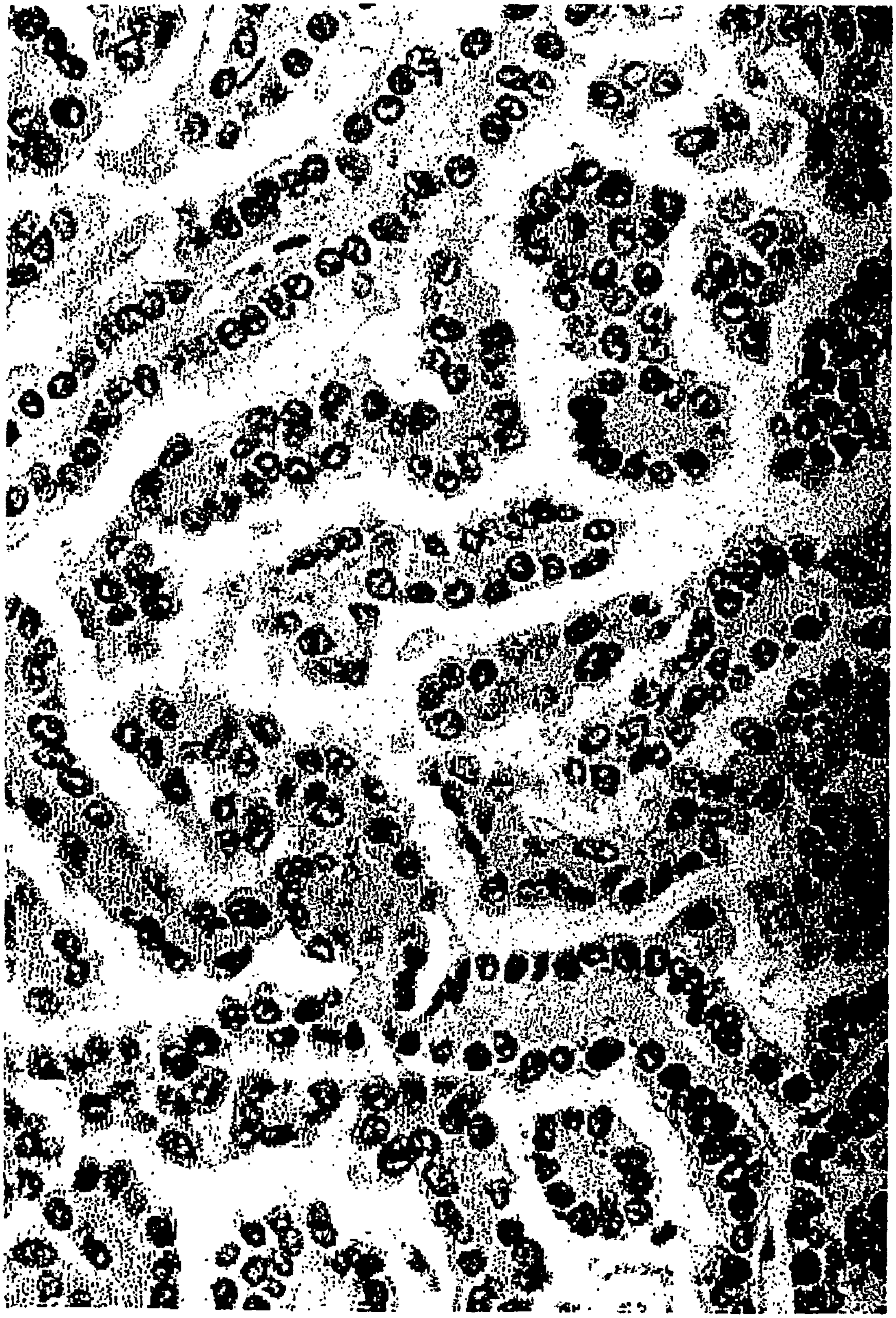
FIG. 1B: High power magnification of photomicrograph of Sparky's lung shows a single cell layer of transformed Type II pneumocytes in a bronchioloalveolar pattern.
Figure 1C:
FIG. 1C: SPARKY-X, the nude/Scid mouse xenograft derived from SPARKY, maintains a bronchioloalveolar pattern even in the mouse.

Sparky the cat was found to have PAC/BAC with extensive lobar involvement. Sections of Sparky's lung revealed extensive replacement of pulmonary parenchyma by BAC which grew in a lepidic pattern along alveolar septae (FIG. 1A; FIG. 1B). The cell line from the malignant pleural effusion has been successfully passed over 30 times, grows as a monolayer in cell culture and exhibits large secretory cytoplasmic vacuoles. The cell line when injected into nude and Scid (SPARKY-X) mice is fully tumorigenic and forms nodules which exhibit a lepidic (BAC) growth pattern even when injected subcutaneously (FIG. 1C). This provides evidence that the lepidic or alveolar growth pattern characteristic of BAC is an inherent property of the transformed Type II pneumocyte and is apparently not related to the presence of pre-existing alveolar spaces within lung parenchyma. The cell line ultrastructurally contains lamellar bodies and exhibits by Northern blot surfactant transcripts. Sparky's tumor, the derived cell line (SPARKY) and the derived xenograft (SPARKY-X) all showed intense immunoreactivity to APO A1, a monoclonal antibody to surfactant. SPARKY was further studied for proof of feline origin with feline specific genomic probes and proof of unique identity with DNA fingerprinting. SPARKY was also studied with flow cytometry and a detailed karyotype analysis. SPARKY was also studied for specific mutations in key genes by PCR followed by sequencing.

Figure 2:
FIG. 2: A computer enhanced R-banded feline BAC cell line karyotype. The modal number is 66. Most abnormalities are numerical. The arrows indicate some structural aberrations including an addition of a dark band on the p-arm of an A2 chromosome, an inversion and deletion in one copy of a C1 chromosome.

SPARKY's genome is clearly feline and exhibits a unique DNA fingerprint. SPARKY was aneuploid by flow cytometric examination and also aneuploid by detailed karyotype analysis (66 chromosomes: 38=normal feline diploid) FIG. 2). Sparky's tumor, the derived cell line (SPARKY) and the derived xenograft (SPARKY-X all showed intense immunoreactivity to monoclonal antibodies to p53. PCR-sequencing analysis of the p53 and Ha-ras and Ki-ras genes showed a G to T transversion at codon 167 (Arginine→Leucine), the feline equivalent of human codon 175, one of the many hot spots mutated in lung cancers of smokers. Ha-ras and Ki-ras were not altered.

Interestingly, as shown in FIG. 3A, SPARKY expressed by RT-PCR retroviral gag transcripts which were 91.7% identical to exogenous JSRV (jaagsiekte retrovirus), the retroviral cause of sheep BAC (for a description of jaagsiekte retrovirus, see, e.g. Palmarini et al., J Natl Cancer Inst 2001 Nov. 7;93(21):1603–14; Palmarini et al., Trends Microbiol. 1997 Dec.;5(12):478–83; DeMartini et al., Vet Clin North Aim Food Anim Pract. 1997 Mar.;13(1):55–70; and Hecht et al., Br Vet J. 1996 Jul.;152(4):395409). None of the base pair differences in these transcripts resulted in an amino acid substitution (FIG. 3B). The feline transcripts of SPARKY, like the exogenous JSRV retroviral transcripts, contained a Sca I site (FIG. 3A). Although feline BAC nay have a different etiology, the molecular alterations it shares with sheep and human lung cancer provide evidence of an overlapping pathway of tumorigenesis.

Immune Deficient Animal Hosts For Practicing Embodiments of the Invention

Severe combined immune deficient (SCID) mice are the preferred animal host utilized in the practice of certain embodiments of the invention. Various other immune deficient mice, rodents or animals may be used, including those which are deficient as a result of a genetic defect, which may be naturally occurring or induced, such as, for example, nude mice, Rag 1 and/or Rag 2 mice, and the like, and mice which have been cross-bred with these mice and have an immunocompromised background. The deficiency may be, for example, as a result of a genetic defect in recombination, a genetically defective thymus or a defective T-cell receptor region. Induced immune deficiency may be as a result of administration of an immunosuppressant, e.g. cyclosporin, removal of the thymus, etc. Various transgenic immune deficient mice are currently available or can be developed in accordance with conventional techniques. Ideally, the immune deficient mouse will have a defect which inhibits maturation of lymphocytes, particularly lacking the ability to rearrange the T-cell receptor region. In one embodiment, C17 scid/scid mice are used. In addition to mice, immune deficient rats or similar rodents may also be employed in the practice of the invention.

Xenograft Animal Models that Simulate Lung Cancer

Embodiments of the invention provide murine xenograft models which simulate or mic bronchioloalveolar carcinoma from primary tumor formation. Also provided are methods for propagating bronchioloalveolar carcinoma tissue as subcutaneous xenografts in immune deficient mice. In the practice of the invention, bronchioloalveolar carcinoma xenografts may be established in immune deficient mice by the subcutaneous implantation of fresh bronchioloalveolar carcinoma explants surgically removed from mammals with bronchioloalveolar carcinomas. The site of implantation may be into any subcutaneous site which will permit blood supply to reach the implant, such as the flanks of the host animal. Tissue from primary bronchioloalveolar carcinomas as well as from sites of lymph node, lung, bone, and other organ metastases may be used to establish the bronchioloalveolar carcinoma xenografts of the invention. Bronchioloalveolar carcinoma explants may be introduced in conjunction with a basement membrane composition, such as Matrigel (U.S. Pat. No. 5,508,188), an extracellular matrix preparation which has been shown to enhance the growth of tumors in vivo (et al., 1993; Noel et al., 1992; Pretlow et al., 1991), as well as other similar types of compositions. Once established, the xenograft tumors grow to considerable size, providing substantial tissue volumes for further use.

Xenografts of the invention retain the clinical phenotype as determined by growth characteristics reflective of the clinical situation.

This and other aspects of the invention described herein provide tools for studying the pathogenesis and treatment of bronchioloalveolar carcinoma. For example, immune deficient mice bearing subcutaneous (and other) xenografts may be used to evaluate the effect of various bronchioloalveolar carcinoma treatments (e.g., therapeutic compositions, gene therapies, immunotherapies, etc.) on the growth of tumors and progression of disease. Xenograft cells may be used to identify novel genes and genes which are differentially expressed in bronchioloalveolar carcinoma cells, or to analyze the effect such genes have on the progression of bronchioloalveolar carcinomas. For example, the genetic compositions of bronchioloalveolar carcinoma cells from xenografts having differing characteristics (e.g. rates of growth and/or aggressiveness) may be compared to each other as well as to the genetic compositions of normal bronchioloalveolar cells. Likewise, the genetic compositions of metastatic bronchioloalveolar carcinoma cells may be compared to those of nonmetastatic bronchioloalveolar carcinoma cells. Various nucleic acid subtraction and sampling techniques may be used for this purpose, including, for example, representational difference analysis (RDA). In addition, bronchioloalveolar carcinoma xenograft cells may be used for the introduction of various genetic capabilities, including the introduction of various genes, antisense sequences, ribozymes, regulatory sequences which enhance or repress the expression of endogenous genes, and so forth.

As discussed in detail below, this aspect of the invention also provides assays for determining the function or effect of various genes on bronchioloalveolar carcinoma cells. In one embodiment, the assay comprises isolating bronchioloalveolar carcinoma cells from a bronchioloalveolar carcinoma xenograft (e.g., subcutaneous or i.p.), transducing the cells with the gene of interest such that the transduced cells express or overexpress the gene, establishing a xenograft tumor in a SCID or other immune deficient mouse with the transduced cells, and evaluating the growth of the resulting xenograft. The effect of expressing the gene on the growth of the xenograft may be determined by reference to a control xenograft established with untransduced bronchioloalveolar carcinoma cells, preferably isolated from the same parental xenograft. In another embodiment, the assay comprises generating a bronchioloalveolar carcinoma xenograft, transducing the cells of the xenograft with the gene of interest in vivo, and evaluating the growth of the xenograft, wherein the effect of the gene on the growth of the xenograft may be determined by reference to a control xenograft.

Similarly, the invention provides assays for determining the effect of candidate therapeutic compositions or treatments on the growth of bronchioloalveolar carcinoma cells. In such contexts, one or more potential therapeutic agents (typically in a composition including a pharmaceutically acceptable carrier) such as chemotherapeutic compounds, antiangiogenic molecules, and known or potential modulators of BAC growth and/or differentiation are administered to the xenograft model (e.g. nude mice harboring the xenograft) and the effects of the agent on tumor growth, metastasis, differentiation etc. are examined and characterized. In addition to examining various therapeutic agents, one can examine the effects of a specific treatment or treatments such as a specific therapeutic regimen (e.g. a specific combination of agents, a specific mode of administration, specific time period or periods of treatment etc.) in an analogous manner. In such embodiments of the invention, the control typically consists of an equivalent xenograft model that has not been exposed to the agent or regimen. In one embodiment, an assay comprises applying the agent composition or treatment to a SCID mouse or other immune deficient mammal bearing a subcutaneous bronchioloalveolar carcinoma xenograft and determining the effect of the treatment on the growth of the xenograft.

Agent compositions for use in the above mentioned embodiments of the invention can be prepared by mixing the desired molecule having the appropriate degree of purity with optional pharmaceutically acceptable carriers, excipients, or stabilizers (*Remington's Pharmaceutical Sciences,* 16th edition, Osol, A. ed. (1980)), in the form of lyophilized formulations, aqueous solutions or aqueous suspensions. Examples of routes of administration include parenteral, e.g., intravenous, intradermal, intramuscular, subcutaneous, oral (e.g., inhalation) transdermal (topical), transmucosal (e.g. a nasal spray), and rectal administration. The agent may also be administered by perfusion techniques, such as isolated tissue perfusion, to exert local therapeutic effects. Solutions or suspensions used for parenteral, intradermal, or subcutaneous application can include the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. Regimens of administration may vary. A single dose or multiple doses of the agent may be used. Such regimens can vary depending on the severity of the disease and the desired outcome. Following administration of an agent to the mammal, the mammal's physiological condition can be monitored in various ways well known to the skilled practitioner familiar with BAC.

Embodiments of the invention also have other clinical applications, including using the model in a method to assess prognosis of a patient with bronchioloalveolar carcinoma. For example, in one embodiment, the method comprises implanting a tumor sample from the patient into an immune deficient mouse subcutaneously, and allowing the implanted sample to grow as a xenograft in the mouse. The rates of xenograft growth may be used as a prognostic indicator. The results of such analysis may assist a treating oncologist in determining how aggressively to treat a patient.

Analytical Methods for Characterizing Bronchioloalveolar Carcinomas

A wide variety of analytical and comparative methodologies for characterizing bronchioloalveolar carcinomas such as the xenografts and/or cell lines disclosed herein are known in the art. For example, gene expression in a xenograft and/or cell line may be measured in a sample directly, for example, by conventional Southern blotting, Northern blotting to quantitate the transcription of mRNA (Thomas, *Proc. Natl. Acad Sci. USA,* 77:5201–5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Alternatively, gene expression may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence polypeptide or against a synthetic peptide based on the DNA sequences provided herein or against exogenous sequence fused to DNA and encoding a specific antibody epitope.

A number of illustrative methods are known in the art that can be used to analyze bronchioloalveolar xenografts and cell lines. For example DNA profiling can be used to distinguish murine from feline DNA and quantitate the murine DNA component of the xenografts, to compare cancerous versus noncancerous bronchioloalveolar cells and to compare various bronchioloalveolar cancer phenotypes (e.g. Aggressive versus nonagressive). Western blot and zymography analysis can be utilized to compare SPARKY-X with non-xenografts with respect to candidate effector molecules. Immunocytochemistry and FISH can also be utilized for this purpose.

In addition, the invention disclosed herein allows one to analyze the pathological features of cancer cells of the bronchioloalveolar lineage, which will lead to better therapies aimed at preventing disease recurrences. In this context, a variety of analytical and comparative methodologies for characterizing the pathological features of cancer cells of the bronchioloalveolar lineage are known in the art.

Methods for Identifying Molecules Associated with the Malignant Phenotype

The invention disclosed herein allows a variety of molecular comparison to identify those genes that are uniquely expressed (or not expressed) by bronchioloalveolar carcinomas to see whether they are associated with oncogenesis and/or the malignant phenotype/genotype. Because bronchioloalveolar carcinoma is a unique disease, unique upstream genes regulate the expression of those effector molecules which cause its phenotype. Therefore one can use methods known in the art to identify the higher level genes which regulate the oncogenic phenotype. In identifying the upstream genes that are uniquely expressed (or not expressed) by bronchioloalveolar carcinomas, one can also investigate whether they trigger separate or common downstream events linked to this pathology.

The xenograft model disclosed herein allows for a variety of different approaches to be used to identify the genetic and phenotypic basis of bronchioloalveolar carcinomas. As discussed in detail below, preferably these approaches involve a comparison of SPARKY-X or SPARKY to noncancerous bronchioloalveolar cells, preferably those of the type II pneumocyte lineage. For example, the invention provides a large number of methods for identifying one or more molecules whose expression is modulated in bronchioloalveolar cancer by determining the level of expression of at least one molecule in a mammalian (e.g. feline) bronchioloalveolar cancer xenograft; and comparing this to the level of expression of the same molecule in a cell having characteristics which are distinct from the human bronchioloalveolar cancer xenograft (e.g. non cancerous bronchioloalveolar cells). In preferred embodiments of this invention, the level of expression of the molecule of the bronchioloalveolar cancer xenograft is determined by a method selected from the group consisting of: Northern Blotting, Southern Blotting, Western Blotting and polymerase chain reaction.

One exemplary approach involves Northern and Western blot comparisons of SPARKY-X to non cancerous bronchioloalveolar cells. As the class of molecules which mediate the phenotype are likely to be either molecules of the adhesion family (either on tumor cells or endothelial cells), growth and differentiation factors (expressed by cancerous cells) or proteolytic enzymes elaborated by tumor cells which facilitate growth one can conduct a comparative screen of the major effector molecules previously implicated in the above mentioned processes (e.g. p53 and k-ras as disclosed herein).

Yet another approach is a mRNA shotgun comparison using microarray libraries. One can then utilize microarray gene chips containing both cloned human or feline secretory molecules and SSTs (secreted sequence tags) which are constructed from a signal trap selection strategy (see e.g. Honjo et al., Science 268: 600–603, (1993)). In this context human and murine secretory microarray chips are available commercially. Therefore, one can carry out a mRNA shotgun comparison of SPARKY-X with non cancerous bronchioloalveolar cells to look for targets that are differentially expressed in SPARKY-X as compared to non-cancerous cells.

Yet another approach involves in vivo subtraction strategies such as those using expanded human recombinant phage libraries. One such approach comprises an in vivo subtraction strategy using expanded human recombinant phage libraries injected into the tail vein of mice harboring SPARKY-X with the anticipated recovery of Ig-phages that selectively bind to SPARKY-X. The power of the immune system stems from its ability to diversify antigen receptors. In the case of B cells, DNA rearrangement combinatory events (i.e., random pairing of heavy and light chains) and specialized "diversity-producing" mechanisms (e.g., N and P nucleotide additions) produces an antibody repertoire of $10^6$ unique molecules. A similar repertoire complexity can be obtained with Ig-phage libraries. Diversity in such libraries can be achieved by the production of semi-synthetic Ig-phage libraries (see e.g. Griffiths et al., EMBO J. 13: 3245–3260 (1994). Semisynthetic phage libraries are created by introducing mutations via error prone polymerase, by reshuffling heavy and light chains, or by randomly mutating the heavy chain complementarity determining region 3 (CDR3) of the Ag binding site. Such manipulation can produce library sizes dose to $10^{13}$. Recent studies have demonstrated the feasibility of injecting a phage library into the tail veins of mice in which selected clones immunolocalize and are able to be recovered from cells such as xenografts (see e.g. Arap et al. Science 279: 377–380 (1998)). This approach is especially suited for our xenograft model because SPARKY-X is present in pleural effusions and hence the injected Ig-phage clones would have easy access to cancer associated antigens. An in vivo subtraction strategy in mice harboring SPARKY-X is preferable because it will eliminate those phages which bind either non-specifically to tumor vasculature or to generally present bronchioloalveolar carcinoma surface antigens or receptors that have nothing to do with the carcinoma phenotype. Following tail vein injection SPARKY-X can be extirpated and bound phages recovered, propagated and re-injected for subsequent rounds of in vivo selection with the ultimate recovery of Ig-phages that selectively bind to surface determinants on either the bronchioloalveolar carcinoma cells or the endothelial cells within SPARKY-X that specifically mediate its phenotype. The cloned phages can be used to identify the surface molecules involved.

The approaches enumerated herein can identify candidate molecules that may play a role in bronchioloalveolar cancers. Once a molecule is identified, one can transduce any candidate molecule which shows promise into non cancerous bronchioloalveolar cells to observe their effect on the phenotype. For example, a nucleic acid (e.g., cDNA or genomic DNA) encoding a candidate molecule may be inserted into a replicable vector for cloning (amplification of the DNA) or for expression. Various vectors are publicly available. The vector may, for example, be in the form of a plasmid, cosmid, vital particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Conversely, through an antisense technology approach one can knock out a molecule of interest that has been identified in SPARKY-X to see if this abolishes its phenotype. Antisense technology entails the administration of exogenous oligonucleotides which bind to a target polynucleotide located within the cells. The term "antisense" refers to the fact that such oligonucleotides are complementary to their intracellular targets. See for example, Jack Cohen, OLIGODEOXYNUCLEOTIDES, Antisense Inhibitors of Gene Expression, CRC Press, 1989; and Synthesis 1:1–5 (1988). Antisense oligonucleotides of the present invention include derivatives such as S-oligonucleotides phosphorothioate derivatives or S-oligos, see, Jack Cohen, supra) which exhibit enhanced cancer cell growth modulatory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer, R. P. et al, J. Org. Chem. 55:4693–4698 (1990); and Iyer, R. P. et al., J. Am. Chem. Soc. 112:1253–1254 (1990), the disclosures of which are fully incorporated by reference herein.

A variety of specific approaches for characterizing bronchioloalveolar cancer cells can be employed utilizing the methods and cells disclosed herein. For example, one can conduct a differential display analysis between the SPARKY-X, SPARKY and normal bronchioloalveolar cells. Preferably one will initially focus exclusively on all or none differentially expressed transcripts between the SPARKYs and the non-SPARKYs in order to identify high level regulatory genes (in the class of oncogenes or tumor suppressor genes) as opposed to downstream genes in this approach. Oncogenes (e.g. by rearrangement) and suppressor genes (e.g. by deletion) will manifest by all or none differential expression of these transcripts, internal consistency between SPARKY-X and SPARKY will provide evidence that these transcripts represent genetic alterations (either amplification, rearrangement or loss), whereas divergence between SPARKY-X and SPARKY will provide evidence that these transcripts are epigenetically rather than genetically regulated and likely not as important from the standpoint of possible oncogenes or suppressor genes. All transcripts identified by differential display can be confirmed by Northern blot of the respective cells cell lines and xenografts. Confirmed transcripts can be excised from the differential display gel, reamplified, cloned and sequenced. Sequences can be compared with known sequences on the BLASTN, expressed sequence tag (dbEST) and The Institute for Human Genome Research (TIGR) databases.

A variety of specific and augmentary procedures for identifying molecules associated with the cancer phenotype are known in the art. For example differential display can be conducted with a third generation RNAimage Kit (GenHUnter Corporation, Nashville, Tenn.) using three one-based-anchored oligo-dT primers to subdivide the mRNA population. With built-in restriction sites at the 5' ends of both anchored and arbitrary 13mers, the longer primer pairs produce highly selective and reproducible cDNA patterns. This ensures that differentially expressed genes are more readily identified, cloned and manipulated. Alternatively one can employ laser capture microdissection. In such methods one can collect fresh frozen cases of carcinoma and successfully microdissect the tumor samples. One can also retrieved archived cases of several hundred carcinomas embedded in paraffin. The availability of such tissue will allow one to determine if the sequences (presence or absence) identified by differential display of SPARKY-X are also exhibited by actual cases of human, carcinoma. Alternatively one can utilize methods for the functional characterization of isolated cDNAs from differential display procedures. In such methods the role of the cDNAs can be determined by first isolating and characterizing their full length cDNA equivalent with RACE and ultimately determining the functional activity of these cDNAs in either SPARKY-X (for transcripts entirely absent in SPARKY-X or the non-cancerous bronchioloalveolar cells (for transcripts exclusively present in SPARKY-X). One can initially continue the sequencing strategy described herein and perform Northern blot hybridization analyses in SPARKY-X and the non-cancerous bronchioloalveolar cells. Once full length cDNAs are isolated, one can use RNase protection assays to determine the fidelity of these cDNAs to ensure that there are no mutations or alterations in these cDNAs resulting from the PCR and RACE procedures. The sequences can then be submitted to NCBI to determine the homology of these cDNAs at the nucleotide and protein levels. The protein sequence will allows one to consider hypotheses on the possible function and activity of the protein as well as generate antibodies to either the purified proteins (proteins could be generated by cDNAs in firm transcribed and translated or bacterial expressed proteins) or synthetic polypeptides. SPARKY-X and the non-cancerous bronchioloalveolar cells can be analyzed at the RNA and protein levels to determine expression levels, cell location, and tissue distribution. SPARKY-X and the non-cancerous bronchioloalveolar cells can be transfected with expression vectors containing these cDNAs in a sense or antisense orientation to determine their effects. Specifically the effects of these cDNAs on the production or inhibition of angiogenic factors and the induction/inhibition of angiogenesis can be assayed in vitro and in mice respectively. Similarly the effects of these cDNAs on the production or inhibition of oncogenesis-related molecules can be assayed in vitro and the induction/inhibition of oncogenesis will be assayed in mice. These studies allow one to determine the cDNA(s)' functional activity and see whether the downstream events they trigger are related to angiogenesis or intravasation or both. If pleoitropism is demonstrated, this provides evidence that the angiogenic and oncogenic phenotypes are on the basis of the same upstream genotype and therefore related.

On the other hand if oncogenesis and its related gene products and angiogenesis and its related effector molecules are separately regulated, this provides evidence that these two phenotypes are distinct.

Using Feline BAC Xenograft and Cell Line Models to Culture and Characterize Common Animal-Human Pathogens Including Those Implicated in Oncogenesis The disclosure herein of established feline xenografts and cells lines that harbor a Jaagsiekte-type tetrovirus provides novel methods for the culture and/or characterization of this virus. In addition, as felines and humans share a group of pathogens (e.g. *pasteurella*, the pathogens of the so-called cat-scratch disease, *trichophyton* and microsporum species, toxoplasmosis, *Cryptosporidium parvum* and *orthopox* viruses etc.), the established feline xenografts and cells lines provide potential culture mediums for common pathogenic agents as well. For example, the parasite *Toxoplasma gondii* is used as one illustrative agent that can be cultured in the disclosed SPARKY cells.

In addition, the disclosure herein of established feline xenografts and cells lines that harbor a Jaagsiekte-type retrovirus provides novel methods, such as those designed to characterize this virus. For example, the disclosure provides evidence that an exogenous retrovirus is involved in either the initiation and/or promotion of human PAC/BAC; that the activation and expression of an endogenous retrovirus and the gene products of this tetrovirus, e.g., gag in human PAC/BAC is an important step in the pathway of tumorigenesis analogous to the activation of oncogenes; and that the mechanism of oncogenesis in human PAC/BAC reactivates retroviral transcripts as downstream events of the neoplasia. These downstream events may have nothing to do with transformation or progression per se but may reflect the end point of a common pathway present in both human PAC/BAC, feline BAC and sheep jaagsiekte (since in jaagsiekte there is also reactivation of endogenous gag). The successful establishment of the first known feline cell line and xenograft of BAC (SPARKY and SPARKY-X) therefore provides a means and model to investigate these possibilities by first determining whether we are dealing with an exogenous or endogenous retrovirus: with the former, attempting to recover the retrovirus from SPARKY/SPARKY-X either by vital particle purification or molecular cloning; with the latter, studying the growth-promoting properties of the endogenous retrovirus and its gene products, e.g., gag, and finally detecting trans factors in feline BAC which activate endogenous retroviral transcription. The findings using SPARKY/SPARKY-X have direct relevance to human BAC/PAC.

The disclosure herein teaches that Jaagsiekte type retrovirus can be present in mammalian BAC cells. In addition, as noted herein, human BAC closely resembles histologically an infectious endemic disease of sheep called jaagsiekte. Consequently, embodiments of the invention include a method of identifying a factor associated with a BAC phenotype by examining a BAC sample for the presence of a transcript that hybridizes under stringent conditions to a mRNA transcript encoding an amino acid sequence shown in FIG. 4. In addition, the invention disclosed herein provides antibodies to proteins such as JSRV-CA and the JSRV amino acid sequences disclosed herein (e.g. FIG. 4).

I. Studies of the Jaagsiekte Retrovirus, JSRV

Previous studies out of the Moredun Research Institute, Scotland, on sheep pulmonary adenomatosis (jaagsiekte), a contagious lung tumour, have indicated that the probable etiological agent is a previously uncultivable type D retrovirus. These studies have succeeded in developing a rapid transmission model for this turnout and produced the first and only permanent jaagsiekte cell lines. Additional studies have clarified the role of retroviruses in contagious tumors of both sheep and goats. These studies have demonstrated unequivocally that an exogenous retrovirus plays a major role in the etiology of jaagsiekte and demonstrated related retroviruses in enzootic nasal tumors of both sheep and goats. These related retroviruses are associated with similar contagious tumors arising from secretory epithelial cells in the respiratory tract and may yield new clues to the mechanisms of oncogenesis in epithelial cells. In cloning the jaagsiekte retrovirus (JSRV), the studies consistently demonstrated that it is important to distinguish the exogenous retrovirus from endogenous retroviral sequences which can also be detected by RT-PCR in normal tissues of sheep. Exogenous retrovirus can be distinguished from these endogenous retroviral sequences in two ways: the exogenous viral transcripts contain a novel ScaI restriction site in a gag gene which is absent in the endogenous sequences and the exogenous retrovirus can be detected with a blocking enzyme-linked immunoadsorbent assay (B-ELISA). This assay depends on the presence of JSRV to inhibit the binding between purified βgal-CA (a fusion protein containing a major capsid protein of JSRV) and the rabbit antiserum to JSRV-CA.

Although human endogenous retroviruses or human endogenous proviral DNAs have been identified in human genomic DNA, this is the first time that JSRV gag has been detected and in the form of an RNA transcript expressed in human and feline BAC. Given that JSRV is the cause of sheep pulmonic adenomatosis or jaagsiekte, a disease with strong histological and biological resemblance to both human and feline BAC, the discovery of JSRV gag transcription is highly significant. This new finding and the use of our feline BAC model serves as the basis for a number of research strategies, including those described below.

Using methods known in the art, one can determine if the retroviral gag transcripts represent an exogenous or an endogenous retrovirus. It can be reasoned that since the sequences of our gag transcripts varied a bit from human individual cases of PAC/BAC and feline BAC, this suggests that we are dealing with an exogenous retrovirus. An endogenous retrovirus would be expected to be conserved and not vary from case to case. However another possibility is that there are several different endogenous retroviral sequences present within the human and feline genome and that we have amplified only a single one but a different one in each case of human PAC/BAC and feline BAC. To determine which of these possibilities is correct, we first need to resolve whether we are dealing with an exogenous or endogenous tetrovirus. The resolution of this question will influence subsequent strategies.

In light of data concerning the presence by RT-PCR of gag transcripts in cases of human PAC/BAC and feline BAC which are also immunoreactive for JSRV-CA, our findings provide evidence that an exogenous retrovirus is involved in either the initiation and/or promotion of human BAC. Moreover, our findings provide evidence that the activation and expression of an endogenous retrovirus and the gene products of this retrovirus, e.g., gag in human PAC/BAC is an important step in the pathway of tumorigenesis analogous to the activation of oncogenes. In addition, our findings provide evidence that the mechanism of oncogenesis in human PAC/BAC reactivates retroviral transcripts as downstream events of the neoplasia. Without being bound by any specific theory, these downstream events may have nothing to do with transformation or progression pet se but may reflect the end point of a common pathway present in both BAC and sheep jaagsiekte (since in sheep jaagsiekte there is also reactivation of endogenous gag).

Using the feline BAC xenograft and cell line and the disclosure provided herein, one can address each of these possibilities by first determining whether we are dealing with an exogenous or an endogenous retrovirus. A number of procedural steps can be undertaken to address this. If dealing with an exogenous virus, one skilled in the art can undertake a first step of recovering a tetrovirus from feline BAC either by a cloning sequence approach or by purifying retroviral particles. If dealing with an exogenous virus, one skilled in the art can undertake a second step of characterizing the growth-promoting or transforming abilities of the endogenous retrovirus and its gene products (e.g. gag) and a third step of Detect trans factors in feline BAC which activate endogenous retroviral transcription. Such procedural steps are discussed in detail below.

A. Exogenous v Endogenous Retrovirus

We plan to use the 229 bp gag as a probe to do a Southern blot on JSRV positive BAC and adjacent JSRV-negative normal lung tissues from both humans and the SPARKY tumor. With this approach there will be three possible scenarios:

In a first scenario, the BAC tumoral tissue is positive and the adjacent lung is negative. This is the best scenario because it supports the presence of an exogenous retrovirus. If this is the case, one can use our 229 bp gag probe and screen a cDNA library (preferably) or a genomic library made from our JSRV positive BAC and clone the complete viral sequence. Or one can use the viral particle approach enumerated in methodology #1 below.

In a second scenario, the tumoral tissue is negative and the adjacent lung is negative. This will be disappointing because it means that the viral copy numbers are so low (not in every tumor cell) that they can be only detected by RT-PCR. Our approach will be to amplify other regions of the retrovirus and clone it.

In a third scenario, the tumoral tissue is positive and the adjacent lung positive. This means that we are likely dealing with an endogenous retrovirus rather than an exogenous one. This situation also exists in jaagsiekte or sheep pulmonic adenomatosis where there is reactivation of a number of endogenous JSRV retroviral transcripts which may play a role in tumorigenesis. If this scenario turns out to be the case, studies proposed in methodology #2 and methodology #3, below will be especially relevant.

Methodology #1: Recovery of a Tetrovirus from Human and Feline BAC Either by a Cloning Sequence Approach or by Purifying Retroviral Particles.

A) Cloning Sequence Approach

Just as we conducted RT-PCR with primers of gag, we plan to see whether we can detect transcripts of pol and env. We anticipate that pol will be present and highly conserved but that env will show some divergence. If we are successful we plan to use a nested primer approach and PCR the entire retroviral transcript. Because we have the advantage of having several hundred grams of fresh frozen tissue available from human cases of BAC and SPARKY-X which are JSRV positive by both immunocytochemistry and RT-PCR, one can attempt to isolate an exogenous retrovirus from this tissue with the following approach.

B) Viral Particle Purification Approach

SPARKY-X and those cases of human BAC that give a positive reaction by immunohistochemistry and reveal JSRV transcripts (preferably with a ScaI site) by RT-PCR and which abundant fresh-frozen tissue is available can be examined further to identify the putative virus particles according to protocols that have been used successfully to detect retroviruses in sheep and goat respiratory tumours (Herring et al., Veterinary Microbiology 1983; 8: 237–249; Sharp et al., J of General Virology 1983; 64: 2323–2327; De Las Heras et al., J of General Virology 1991: 72: 2533–2535; De Las Heras et al., Veterinary Record 1993; 132: 441; Palmarini et al., J of General Virology 1995: 76: 2731–2737). Briefly, tumours can be homogenized (10% w/v suspension in TNE(10 mM Tris, 100 mM NaCl, 1 in M EDTA)) and clarified by centrifugation at 10,000 g/1 h/4° C. The supernatant can be removed and further centrifuged at 100,000×g through a double layer of glycerol (25% and 50% v/v) for 1 h at 4° C. The supernate can be removed and the pellet resuspended as a 200 times concentrate in TNE buffer. The pellets can examined for retrovirus by western blotting as described (Sharp et al., J of General Virology 1983; 64: 2323–2327) using the antiserum to JSRV CA. Any samples that produce a positive result, indicated by a band of approximate Mr 25–27000 reacting with the antiserum to JSRV CA, can be analyzed further by isopycnic centrifugation on 20% to 55% (w/w) sucrose gradients. The gradients can be fractionated and each 0.5 ml fraction resuspended in 4.5 ml TNE buffer, centrifuged at 100,000×g/1 h/4° C. and the resultant pellet resuspended in 100 μl TNE. These fractions can be examined for retrovirus by western blotting as described above. If a positive result is obtained only in fractions with densities characteristic of retroviruses, this will support the notion that an exogenous retrovirus is present in these human tumours and attempts can be made to clone/sequence the genome of this virus from this fraction.

Using methods known in the art one can pursue a similar approach in attempting to identify putative retroviral particles from the feline BAC cell line and xenograft. In addition to attempting to isolate viral particles from a homogenate of both cell pellet and xenograft, one can use both concentrated conditioned media (concentrated 1000 fold using Centriprep-10 concentrators (Amicon, Beverly, Mass.) and concentrated pleural effusions from BAC tail vein-inoculated Scid mice. This latter approach may prove more successful in isolating virus because in the jaagsiekte experiments we found that the virus could be more readily isolated from bronchial and nasal discharge material than from actual tumoral lung tissue. Even though the feline BAC cell line and xenograft contain no evidence of retroviruses on ultrastructural studies we are not discouraged by this fact alone because most cases of both natural as well as experimentally-induced jaagsiekte do not show viral particles within tumor cells. If we find evidence of retrovirus in the xenografts one can be cautious in interpreting these results because we know that nude and Scid mouse xenografts can be secondarily infected with murine retroviruses. Whether the retrovirus is the JSRV retrovirus can be determined by sequencing.

If an exogenous retrovirus appears to be involved, using methods known in the art one can collect sera prospectively from patients with PAC/BAC and screening their sera by Western blot for antibodies against JSRV-CA. If an exogenous retrovirus appears not to be involved in either the initiation and/or promotion of human/feline BAC, then activation and expression of an endogenous retrovirus and the gene products of this retrovirus, e.g. gag or some other retroviral gene product in human PAC/BAC may nevertheless be an important step in the pathway of tumorigenesis analogous to the activation of oncogenes. For example, in breast cancer, the int oncogenes were identified solely by their association with mouse mammary tumor virus (MMTV)-induced mammary tumors in mice and at least one of these oncogenes, int-2, was found to be activated in some human breast cancers and yet MMTV does not play a role in human breast cancer. The proposal, in Methodology #2, will examine this possibility.

Methodology #2: Study the Growth-Promoting or Transforming Abilities of the Endogenous Retrovirus and Its Gene Products, e.g. gag Using methods known in the art one can screen a series of human PAC/BAC lines obtained from ATCC and other sources to identify lines that express JSRV gag so that we can work with these as well as our feline BAC line. This approach can utilize both sense and antisense strategies with JSRV gag and other retroviral genes. One can use recipient human and feline BAC lines some of which are JSRV positive and some JSRV negative. Other non-BAC lines, e.g. squamous cell carcinoma can also be used. One can transfect both out JSRV negative/positive cell lines with both sense and antisense gag constructs appropriately. One can initially transfect with electroporation and select the transfectants by G418 resistance. The plasmid construct (pBK-CMV), a eukaryotic expression vectors containing gag cDNA under the control of a CMV promoter as well as G418 selection can be used. We have determined that with this approach our recipient cell lines exhibit a moderate to high transfection efficiency of $10^{-4}$ and each successfully transfected clone averages between 4–10 plasmid copy number.

Screening for successfully transfected clones can be carried out using our antibodies against JSRV-CA. In the case of antisense transfection we would of course be looking at a recipient cell line which was initially JSRV positive whose transfected subclone became JSRV negative. In the case of sense transfection we would be looking for exactly the opposite. RT-PCR could also be used but it is not as good as antibody screening.

The JSRV positive and negative clones (as a result of transfection) can be compared to the natural JSRV positive and negative clones with respect to growth parameters (tumor cell doubling time, plating efficiency, saturation density, etc.), tumorigenicity, latency, in vivo growth rate and metastasis. The retroviral gag and other cDNAs which are isolated can also be cloned into inducible expression vectors (either using a modified metallothionine, pSV2M(2) 6, or a lactose operon promoter, pOP13) as an inducible model to investigate the role of these cDNAs as upstream inducers of other genes related to tumor progression of BAC. We would then be able to eventually use subtraction hybridization techniques to isolate the genes that are altered downstream and possibly identify an intracellular pathway which is affected by retroviral gene expression.

Using methods known in the art our strategy is fairly straightforward. However, if this approach fails to demonstrate that gag or other retroviral gene products promotes growth or transformation, a third hypothesis is that the mechanism of oncogenesis in human and/or feline BAC reactivates endogenous retroviral transcripts as downstream events of the neoplasia. These downstream events have nothing to do with transformation or progression per se but may reflect the end point of a common pathway present in both human and feline BAC and sheep jaagsiekte (since in sheep jaagsiekte there is also reactivation of endogenous retroviral sequences). This common pathway may be pivotal for tumor progression in all three diseases. Therefore the activation of endogenous retroviral transcription may serve as a marker for a more generalized pathway of tumor progression in feline, human, and ovine BAC. Methodology #3 is designed to examine this latter hypothesis.

Methodology #3: Detection of Trans Factors in Human and Feline BAC which Activate Endogenous Retroviral Transcription In this approach one can use the JSRV positive feline line (SPARKY) and JSRV positive and negative human cell lines of BAC. One can obtain a clone of the JSRV retrovirus from the Moredun Institute. From this clone one can construct LTR promoter-CAT constructs. In this approach, transfection studies with these constructs can be conducted to identify both enhancer and silencer cis elements present in the retroviral LTR. These cs elements can be used to identify trans-acting factors that enhance retroviral expression in the JSRV positive cell lines and suppress JSRV expression in the JSRV negative cell lines. All lines can be transfected with the LTR-CAT constructs and CAT protein can be measured. The transfected cells can be standardized by co-transfection with a β-galactosidase expression vector, pCH110. This can allow us to determine the overall activities of JSRV in these cells. We anticipate that reporter levels can initially reflect the constitutive levels of JSRV expression in the respective lines. However as we identify different domains of the LTR promoter in particular, we may be able to identify silencer elements by comparative reduction in CAT levels. Gel mobility shift analyses can then be done. Again the strength of our approach is our use of JSRV positive (where LTR-CAT should be high) and negative cell lines (where LTR-CAT should be low). In the gel mobility shift assays nuclear cell extracts from the different lines can be compared to each other and to HeLa cells (control protein) (Stratagene, La Jolla, Calif.). If any transcription factor(s) are being expressed in the JSRV positive cell lines and not the JSRV negative cell lines, we would be able to determine this using these experiments.

If specific DNA-binding proteins are detected by the above studies their precise sequence affinities can be determined by DNA footprinting experiments. Any protected sites localized and sequenced by these methods can be compared to described consensus sequences known to be present in other promoters. Confirmation of sites thus defined can be performed by the use of synthetic oligonucleotides containing the putative control sequence to titrate off the specific DNA binding protein(s). Finally an oligonucleotide affinity column can be used to purify the specific DNA binding protein(s) identified. Using an alternate approach for identifying the trans-acting factors, we may be able to use these specific oligonucleotides to screen bacterial expression libraries separately made from cDNA from JSRV positive BAC cell lines compared to JSRV negative cell lines. Any cDNAs isolated from the expression library can be sequenced/compared to known sequences. The ability of any cDNA to enhance tumorigenicity, growth, etc can be investigated in an approach similar to that of Methodology #2.

With the use of these mentioned approaches to define the as-acting elements in the LTR regulatory regions under carefully controlled conditions, it is expected that spurious localization of responsive elements would be minimized. We could also use RNase protection techniques to confirm that increased CAT protein is due to increased CAT RNA.

II. Characterization and Culturing *Toxoplasma gondii*

*Toxoplasma gondii* is an intracellular protozoan parasite of worldwide distribution. Currently, parasites that harbor a complete antigenic profile, that is necessary for the serological diagnosis of human *Toxoplasma* infections, are provided by in vivo culture methods only. Thus, in most laboratories the asexual proliferative stage of the parasite, the tachyzoite, is maintained by successive intraperitoneal passages in highly susceptible animals such as mice. For references on the culture of *Toxoplasma gondii*, see also Klien et al., ALTEX 1998 15(5): 37–39; Ashburn et al., J Clin Pathol 2000 53(8): 630-3; Evans et al., Eur. J. Clin. Microbiol. Infect. Dis. 1999 18(2): 879–84; Creuzet et al., Parasitol. Res. 1998 84(1): 25–30; Sahm et al., Parasitol. Res. 1997 83(7): 659–65; Fischer et al., Parasitol. Res. 1997 83(7): 637–41; James et al., J Clin Microbiol 1996 34(6): 1572–5; Weiss et al., J. Eukaryot Microbiol. 1995 42(2): 150–7 and Couzinet et al., Exp. Parasitol. 1994 78(4): 341–51.

Improved in vitro methods to provide sufficient amounts of high quality parasite antigen suitable for methods such as vaccine development and production is desirable. The invention provide herein allows for a variety of methodological strategies including the growth of Toxoplasmosis in vitro in SPARKY, the growth of Toxoplasmosis in vivo in SPARKY-X in mice and the growth and purification of toxoplasmosis in sufficiently large quantities to develop a vaccine.

A typical embodiment of the invention consists of using SPARKY and/or SPARKY-X to culture Toxoplasmosis in vivo and/or in vitro by exposing a culture of SPARKY to Toxoplasmosis sufficient to infect the cells and then culturing the cells under conditions that permit the growth of Toxoplasmosis. Typical culture conditions for propagating Toxoplasmosis are described above and skilled artisans can readily adapt such methods for use with SPARKY and SPARKY-X.

Illustrative Embodiments of the Invention

The invention disclosed herein has a number of embodiments. A preferred embodiment of the invention is a mammalian bronchioloalveolar xenograft having the biological characteristics of the xenograft designated SPARKY-X as described in ATCC patent deposit designation PTA-2920 such that the xenograft grows within an immunocompromised host in a lepidic bronchioloalveolar carcinoma growth pattern. In highly preferred embodiments, the xenograft is of the type II pneumocyte lineage. In related embodiments, the xenograft expresses a mRNA transcript that encodes a protein having an amino acid sequence that has at least a 90% identity to the jaagsiekte retrovirus gag amino acid sequence shown in SEQ ID NO: 19. A specific embodiment of the invention is a feline lung cancer xenograft designated SPARKY-X as described in ATCC patent deposit No. PTA-2920.

Yet another embodiment of the invention is a feline bronchioloalveolar cell line having the biological characteristics of the cell line designated SPARKY as described in ATCC patent deposit designation PTA-2919 such that the xenograft exhibits surfactant expression as shown by Northern blot and exhibits lamellar bodies ultrastructurally. Typically the cell line expresses a mRNA transcript that encodes a protein having at least a 90% identity to the jaagsiekte retrovirus gag amino acid sequence shown in SEQ ID NO: 19. A specific embodiment of the invention is a feline lung cancer cell line designated SPARKY as described in ATCC patent deposit No. PTA-2919.

Yet another embodiment of the invention is a method of generating a SPARKY-X type xenograft by obtaining a sample of bronchioloalveolar cells from the pleural effusion of a mammal having a bronchioloalveolar carcinoma, implanting the cells from the sample into an immunocompromised mammalian host, and then identifying the xenograft growing in the immunocompromised mammalian host Another embodiment of the invention is a non-human animal model for bronchioloalveolar carcinoma comprising an immunocompromised host animal inoculated with a mammalian bronchioloalveolar xenograft having the biological characteristics of the xenograft designated SPARKY-X as described in ATCC patent deposit designation PTA-2920 such that the xenograft grows within an immunocompromised host in a lepidic bronchioloalveolar carcinoma growth pattern. Typically the immunocompromised host animal is a nude mouse. Preferably the mammalian bronchioloalveolar xenograft is the xenograft designated SPARKY-X as described in ATCC patent deposit No. PTA-2920.

Yet another embodiment of the invention is an assay for assessing the effect of a treatment for bronchioloalveolar carcinoma by applying the treatment to an immune deficient mouse bearing a bronchioloalveolar carcinoma xenograft generated by implanting bronchioloalveolar carcinoma tissue or a cell suspension thereof from a mammal in the immune deficient mouse and then determining the effect of the treatment on the growth of the xenograft in said mouse. In such assays the treatment typically comprises administering a therapeutic agent to the immune deficient mouse such as a nude mouse. Preferably the mammalian bronchioloalveolar xenograft is the xenograft designated SPARKY-X as described in ATCC patent deposit No. PTA-2920.

Another embodiment of the invention is a method of identifying a mRNA transcript whose expression is modulated in bronchioloalveolar carcinoma by providing a mammalian bronchioloalveolar xenograft having the biological characteristics of the xenograft designated SPARKY-X as described in ATCC patent deposit designation PTA-2920 such that the xenograft grows within an immunocompromised host in a lepidic bronchioloalveolar carcinoma growth pattern, determining the level of expression of at least one mRNA transcript in the mammalian bronchioloalveolar xenograft, and then comparing the level expression of the mRNA transcript in the mammalian bronchioloalveolar xenograft to the level of expression of the mRNA transcript in a mammalian bronchioloalveolar cell isolated from a mammal that does not suffer from bronchioloalveolar carcinoma. Typically the level of expression of the mRNA of the bronchioloalveolar carcinoma xenograft is determined by Northern Blotting or polymerase chain reaction. Preferably the mammalian bronchioloalveolar xenograft is the xenograft designated SPARKY-X as described in ATCC patent deposit No. PTA-2920.

A related embodiment of the invention is a method of identifying a mRNA transcript whose expression is modulated in bronchioloalveolar carcinoma by determining the level of expression of at least one mRNA transcript in the feline lung cancer cell line designated SPARKY as described in ATCC patent deposit No. PTA-2919, and then comparing the level expression of the mRNA transcript in the feline lung cancer cell line to the level of expression of the mRNA transcript in a feline bronchioloalveolar cell isolated from a feline that does not suffer from bronchioloalveolar carcinoma.

Another preferred embodiment of the invention is a method of simulating the progression of bronchioloalveolar carcinoma from primary tumor formation to metastasis in an animal model by generating a bronchioloalveolar carcinoma xenograft in an immune deficient mouse by implanting malignant pleural effusion of a BAC bronchioloalveolar carcinoma, or a cell suspension thereof from a mammal into an immune deficient mouse and allowing the xenograft to grow for a time sufficient to permit the detection of bronchioloalveolar carcinoma cells within and/or external to the implant site in the immune deficient mouse thereby simulating the progression of bronchioloalveolar carcinoma from primary tumor formation to metastasis in the animal model.

Yet another embodiment of the invention is an assay for assessing the effect of a treatment for bronchioloalveolar carcinoma by applying the treatment to an immune deficient mouse bearing a bronchioloalveolar carcinoma xenograft generated by implanting bronchioloalveolar carcinoma tissue or a cell suspension thereof from a mammal in the immune deficient mouse and then determining the effect of the treatment on the growth of the xenograft in said mouse.

Yet another embodiment of the invention is an assay for assessing the effect of a gene of interest on bronchioloalveolar carcinoma by introducing the gene to an immune deficient mouse bearing a subcutaneous bronchioloalveolar carcinoma xenograft generated by implanting bronchioloalveolar carcinoma tissue or a cell suspension the immune deficient mouse, transducing the cells of the xenograft with the gene in vivo, evaluating the presence of metastasis in the immune deficient mouse by detecting bronchioloalveolar carcinoma cells in the peripheral blood, bone marrow, lymph nodes or other sites distant from the site of the subcutaneous xenograft, wherein the effect of the gene on the progression of bronchioloalveolar carcinoma is determined by reference to a control immune deficient mouse bearing a subcutaneous human lung xenograft generated with an untransduced subset of the cells of the xenograft. Yet another embodiment of the invention is an a chimeric mouse model of bronchioloalveolar carcinoma, said mouse model having a bronchioloalveolar carcinoma xenograft, wherein the xenograft in the mouse model exhibits a lepidic or alveolar growth pattern characteristic of BAC.

The present invention is further detailed in the following Examples, which are offered by way of illustration and are not intended to limit the invention in any manner.

Throughout this application various articles, patents, patent applications, and other publications etc. are referenced. The disclosures of these publications etc. are hereby incorporated by reference herein in their entireties. Certain portions of these incorporated publications etc. may be disclosed for purposes of providing a full, dear and concise written description of the various aspects of the embodiments of the invention.

Deposit of Material

The following materials have been deposited with the American Type Culture Collection, 10801 University Boulevard, Manassas, Va. 20110–2209, USA (ATCC):

| Material | ATCC Dep. No. | Deposit Date |
|---|---|---|
| SPARKY | PTA-2919 | Jan. 19, 2001 |
| SPARKY-X | PTA-2920 | Jan. 19, 2001 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit.

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

Example 1

Materials and Methods For Characterizing BAC

Total RNA extracted from the BAC cell line was reverse transcribed using an oligo dT primer (Superscript™, Life Technologies) and then PCR amplified using primers for the feline p53, Hras, K-ras, and N-ras genes as follows:

p53 (1)

```
AS: 5'-GGCGCCTATGGTTTCCATTTAG-3'   (SEQ ID NO: 3)
DR: 5'-CATCCAGTGGCTTCTTCTTTTG-3'   (SEQ ID NO: 4)
```

K-ras (5)

```
IaS:     5' GACTGAATATAAACTTGTGG 3'  (SEQ ID NO: 5)
IIaAS:   5' CTATAATGGTGAATATCTTC 3'  (SEQ ID NO: 6)
```

H-ras (5)

```
IaS:     5'-GACGGAATATAAGCTGGT-3'    (SEQ ID NO: 7)
IIaAS:   5'-CCTGTACTGGTGGATGTCC-3'   (SEQ ID NO: 8)
```

N-ras (6)

```
IaS:     5'-GACTGAGTACAAACTGGTGG-3' (SEQ ID NO: 9)
IIaAS:   5'-CTGTAGAGGTTAATATCCGC-3' (SEQ ID NO: 10)
```

Conditions of PCR: PCR reactions were performed in 100 microliters containing 1× buffer (20 mM Tris-HCl (H 8.4), 50 mM KCl), 1.5 mM MgC12, 200 micromolar dNTPs, 200 nM primers and 5 Units of Taq polymerase (Boehringer Mannheim). Cycling for the p53 gene was 30 cycles of 94° C. (1'), 60° C. (1.5'), and 72° C. (2'). The ras genes were similarly amplified for 35 cycles using a 50° C. (H-ras and K-ras) or 55° C. (N-ras) annealing temperature. DNA sequence analysis was performed on an ABI DNA Sequencer Model 377 using 0.1 micrograms of gel purified DNA as template for 3.3 pmoles of sense or anti-sense primer. Amplified p53 gene segments were also cloned into a Bluescript plasmid (Stratagene) prior to sequencing studies.

The feline p53 primers amplified a 664 by fragment of coding sequence (codons 97–318, exons 4–9) (Okuda et al.,. Int. J. Cancer 58, 602–607 (1994); Okuda et al., J. Vet. Med. Sci. 55(5): 801–805 (1993); Mayr et al., Br. Vet J. 151, 707–713 (1995); Mayr et al., Br. Vet J. 151,325–329 (1995)).

The H-ras, K-ras, and N-ras primers amplified 285, 289, or 289 bps, respectively, of exons I and II which contain the mutational hot spot codons 12, 13, and 61 (Watzinger et al., Mamm. Genome 9(3): 214–219 (1998); Watzinger et al., Cancer Res. 54: 3934–3938 (1994)).

Summary: DNA sequence analysis of PCR-derived DNA and plasmid cloned DNA of the 664 by fragment the p53 gene repeatedly identified a G:C to T:A transversion (Arg to Leu) at codon 167 in the BAC cell line, a feline codon correlate of one of the mutational hot spots reported in human cancers (Okuda et al.,. Int. J. Cancer 58, 602–607 (1994)). A silent mutation was also seen at codon 155 (C:G to T:A), but sequence of normal feline RNA revealed the same change from the previously published sequence. Sequencing studies identified no missense mutations in the H-ras and K-ras genes. Attempts at amplifying the N-ras gene with primers flanking the first two exons yielded a PCR product whose sequence matched the previously reported feline N-ras pseudogene sequence (Watzinger et al., Mamm. Genome 9(3): 214–219 (1998)). Efforts to specifically amplify the wild type sequence from total RNA were unsuccessful using the above primers.

Cytogenetics We prepared metaphase slides of the Feline BAC cell line with a standard technique (Lee et al., M. J. Barch (ed.), The ACT Cytogenetics Laboratory Manual pp. 107–148, New York: Raven Press. 1991). Briefly, Colcemid (0.1 ug/ml final concentration) was added when cultures were 70–80% confluent. Cells were harvested at 30 minutes, 1 hour, and 2 hours following addition of coloemid. We varied the time in colcemid to optimize degree of condensation of metaphase chromosomes for the purpose of karyotyping. Cells were trypsinized, centrifuged, and the pellet was suspended in hypotonic (0.075 M) KCl for 15 minutes. Following a second centrifugation, cells were fixed in 3:1 methanol: acetic acid. The cell pellet was diluted in the fixing solution to allow appropriate cell concentration and spreading of chromosomes when dropped on microscope slides. Slides were dried and aged for at least one week.

To confirm feline origin, we performed FISH with total feline genomic DNA as a probe. DNA was extracted from the blood lymphocytes of a “normal” cat was used to create the probe using degenerative oligonucleotide-primed polymerase chain reaction (DOP-PCR) with digoxigenin-conjugated dUTP (Telenius et al., Genes, Chromosomes & Cancer, 4: 257–263, 1992; Telenius et al., Genomics, 13: 718–725, 1992). Labeled DNA was mixed with 50% formamide, 2×SSC, and 10% dextran sulfate, denatured for 10 minutes at 72° C., and preannealed at 37° C. for 45 minutes. No blocking DNA was used. We then allowed the probe to hybridize for 24 hours at 37° C. to denatured metaphase cells from i) the feline BAC cell line, ii) normal feline lymphocytes (positive control), and iii) normal human lymphocytes (negative control). The slides were washed at 45° C. in 1) 50% Formammide/2×SSC, 2) 2×SSC, 3) 0.1×SSC for 10 minutes each. Slides were then rinsed in room temperature PBD. Slides were treated with FITC-conjugated anti-digoxigenin antibody. Slides were visualized using a Zeiss Axioskop fluorescent microscope.

Chromosomal abnormalities were characterized using a novel method of computer enhanced fluorescent R-banding, developed in our lab (Christian et al., Cytogenetics and Cell Genetics, 82: 1998). In this procedure, metaphase preparations of feline BAC were banded with 4', 6-diamino-2-phenyl-indole (DAPI), which binds A-T rich regions of DNA and with chromomycin A3, which binds preferentially G-C rich regions. We then captured gray scale images of a metaphase nucleus for each stain using a computerized image analysis system. Following an intensity normalization procedure to account for varying brightness' of the stains, the DAPI image was divided by the Chromomycin image. This technique is similar to that used in CGH. This process gave a high-resolution R-banded pattern unique to each chromosome.

Flow Cytometry. A 70–80% confluent culture of the Feline BAC was trypsinized centrifuged and rinsed in PBS. The cell pellet was then fixed in cold 70% ethanol. The cell solution was refrigerated for one day. The cells were then centrifuged and the pellet was dried briefly. The fixed cells were suspended in propidium iodide. This suspension was filtered to remove cell clumps. Studies were performed with an EPICS V Flow Cytometer.

Results: FISH performed with labeled feline genomic DNA confirms feline origin of the cell line. The modal number is 66 based on counts of 30 metaphases. This compares with a diploid number of 38 in normal feline cells. The fluorescent R-banding used to characterize cytogenetic aberrations resulted in high-resolution bands. Most abnormalities are numerical. There are some structural aberrations including an addition of a dark band on the p-arm of an A2 chromosome, an inversion and deletion in one copy of a C1 chromosome. Flow cytometry confirmed aneuploidy.

Archiving of Human BAC Cases. Previous studies have reviewed and archived all pathologically verified primary lung cancer cases diagnosed at UCLA Medical Center from 1955 to 1990 (Barsky et al., Cancer 1994; 73: 1163–1170; Barsky et al., Modern Path 1994; 7: 633–640). A total of 1527 cases were diagnosed during this time period, 1125 (74%) in men and 402 (26%) in women. A total of 187 cases, representing 12.2% of all lung cancer cases, were classified as bronchioloalveolar carcinoma. In men, 84 cases (7.5%) were of the bronchioloalveolar type. In women, 103 cases (25.6%) were classified as bronchioloalveolar carcinoma. Both the number and proportion of cases classified as bronchioloalveolar lung cancer have increased steadily over each five-year time period. The proportion of bronchioloalveolar carcinomas increased from 5% in 1955–1960 to 11% in 1981–1985. Since that time, the proportion has more than doubled, equaling 23% of all lung cancers in 1986–1990. Bronchioloalveolar carcinoma is now the most common type of lung cancer diagnosed at UCLA, approximately equal in prevalence to squamous cell carcinoma and other adenocarcinomas. Much of this increase in bronchioloalveolar carcinoma has occurred in women, as evidenced by the female predominance. While the male/female ratio of all other cell types shows a steady decline from approximately 7/1 in 1955–1960 to 3/1 in 1986–1990, the male/female ratio for bronchioloalveolar carcinoma has wavered around unity, dropping below unity for the most recent time period Data from UCLA then confirm the increase in bronchioloalveolar carcinoma observed by others (Ikeda et al., Lung cancer 1991; 7:157–164). The cause of this increase in a lung cancer not strongly associated with cigarette smoking is yet to be determined. The cases of human BAC were classified as to centricity as solitary, diffuse or multifocal. At least some of the cases of multifocal BAC were on the basis of multiclonality (Barsky et al., Cancer 1994; 73: 1163–1170; Barsky et al., Modern Path 1994; 7: 633–640). The cases of BAC were also classified according to histology as sclerotic, non-mucinous and mucinous. The non-mucinous cases were further subclassified as Clara, Type II pneumocyte or mixed with the help of additional immunocytochemical and ultrastructural studies. Since 1990, approximately 200 additional cases of human BAC have been collected prospectively and classified. A large majority of these cases have been stored frozen as well as in paraffin. The frozen material has preserved the DNA, RNA, and protein of human BAC. Demographic data is available for most of these cases. Some of these cases reflect very large tumors measuring at least 8 cm in greatest dimension and represent a source of human material ripe for investigative study.

Example 2

Production of Recombinant JSRV Capsid Proteins

Standard molecular biology procedures were used as described (Sambrook J, Fritsch E, Maniatis T. Molecular cloning: 2nd ed., NY: Cold Spring Harbor Lab, 1989). Briefly, the insert fragment, containing a part of the JSRV gag gene (bases 953 to 3030 of the nucleotide sequence (York et al., J of Virology 1992; 66: 4930–4939)) was excised from plasmid pBluescript-Js382 using EcoRI and subcloned into plasmids pMS1S (Sherp A et al., J of Immunological Methods 1990; 128: 81–87) and pGEX1λT (Pharmacia). These constructs were expressed in *E. coli* host strain NM522 as β-galactosidase (βgal-CA, plasmid pMCA) and glutathione-S-transferase (GST-CA, plasmid pGCA) fusion proteins respectively. Confirmation that the gag gene was in the correct reading frame was obtained by sequencing across the vector-insert junction, as well testing clones for production of β-galactosidase and GST fusion proteins of the appropriate size by western blotting (immunoblot) analysis with a goat antiserum to Mason-Pfizer monkey virus major capsid protein (MPMV-CA) (Sharp et al., J of General Virology 1983; 64: 2323–2327). Transformed bacteria were grown and induced with isopropyl β-D-thiogalactopyranoside IPTG) for the expression of recombinant proteins. Bacteria were pelleted (5000×g for 10 min) and resuspended in 20 ml TE (10 nM Tris pH7.5, 1 mM EDTA). Phenylmethylsulphonylfluoride (2 mM) was added before lysing the cell suspension in a French press at 1500 psi (10.35 MPa). The lysate obtained was sonicated and clarified at 100,000×g at 4° C. for 10 min. βgal-CA fusion protein was purified by affinity chromatography using a 4 ml column of aminobenzyl-1-thio-βgalactopyranoside (ABTG) agarose (Sigma) as previously described (Cameron et al., Microbiology 1994; 140: 1977–1982). GST-CA was purified by affinity chromatography using a 4 ml column of glutathione sepharose (Pharmacia) as recommended by the manufacturers. The yield of soluble βgal-CA was approximately 9 mg/l of bacterial culture at about 75% purity as estimated by SDS-PAGE. GST-CA could not be eluted with free glutathione from the Sepharose beads as recommended by the manufacturer and was therefore further used coupled to the beads to immunize rabbits.

Example 3

Production of Rabbit Polyclonal Antiserum to JSRV-CA

A specific rabbit antiserum to JSRV-CA was prepared by immunizing rabbits with 500 μg βgal-CA combined with Freund's incomplete adjuvant. After 15 days the rabbit was boosted with 500 μg of GST-CA bound to the glutathione Sepharose beads. A third injection of GST-CA (500 μg) was given after 4 weeks and the rabbit was bled 15 days after the last injection. By western blotting the rabbit antiserum recognized the two recombinant proteins βgal-CA and GST-CA, as well as the native 25 kDa CA in JSRV. There was no reaction with any other protein in sucrose gradient purified JSRV. Further specificity of this serum for JSRV-CA has been verified extensively in the sheep tumour model, using western blotting, blocking ELISA and immunohistochemistry (Palmarini et al., J of General Virology 1995: 76: 2731–2737). To minimize non-specific reactions, the antiserum may be absorbed overnight at 4° C. with a lysate of IPTG-induced NM522-pMS1S cells. The serum was then centrifuged at 100,000×g/30 min. to pellet any bacterial debris, aliquoted and stored at −20° C. until used. Immunohistochemistry of lung sections of sheep affected by jaagsiekte revealed in the lungs immunopositivity confined to the cytoplasm of the transformed Type II pneumocytes involved in pulmonary adenomatosis. The immunopositivity was confined to the neoplastic cells; adjacent interstitial cells and adjacent untransformed alveolar cells and bronchiolar cells were completely negative.

Example 4

Demonstration of JSRV-Related Antigen in Cases of Human BAC and the Feline BAC Cell Line Antibodies made to a recombinant JSRV major capsid protein of this virus (derived from gag) in our initial immunocytochemical studies surprisingly were able to recognize an immunologically related protein in a significant number of human PAC/BAC cases and in feline BAC but not in other types of lung cancer nor in normal lung. More surprisingly, in our subsequent studies, RT-PCR performed on these PAC/BAC cases revealed expression of JSRV gag transcripts which were 90–100% identical to both the endogenous and exogenous gag transcripts (distinguished by a ScaI site) expressed in sheep jaagsiekte.

Using these rabbit polyclonal antibodies to JSRV-CA, the recombinant JSRV major capsid protein expressed from JSRV gag, we demonstrated intense cytoplasmic immunoreactivity in 23/40 (58/%) cases of non-mucinous BAC, in 17/46 (370%) cases of peripheral adenocarcinoma (PAC) and in 2/15 (130%) mucinous BAC. No cases of squamous cell, small cell, large cell undifferentiated or non-lung carcinomas were positive (0/100 cases). The percentage of JSRV positivity in BAC/PAC increased over the past three decades (15%–50%). We observed both diffuse and focal staining within the transformed Type II pneumocytes/Clara cells. Adjacent lung tissues were non-reactive. The feline BAC tumor, derived cell line (SPARKY) and xenograft (SPARKY-X) also displayed intense focal cytoplasmic JSRV immunoreactivity.

In order to exclude the possibility that the basis of this JSRV immunoreactivity in the human and feline BAC was a cross-reacting protein having nothing to due with the presence of the JSRV major capsid protein, we carried out RT-PCR on the cases of human BAC and the feline BAC cell line that displayed this JSRV immunoreactivity. Cases of human BAC which were JSRV negative and cases of squamous cell carcinoma and small cell carcinoma which were also JSRV negative were also examined by RT-PCR.

Example 5

JSRV-GAG Transcripts by RT-PCR

The genome of the jaagsiekte sheep retrovirus (JSRV) contains the canonical gag env, and pol genes. The JSRV genome is 7462 nucleotides long and contains the canonical gag, pol and env genes, as well as an additional open reading frame (orf-x) that overlaps pol. Reverse transcriptase polymerase chain reaction (RT-PCR) for a 229-bp region internal to the gag gene (position 1598 to 1826) was carried out using primers (P1) and (P2).

```
(P1) sense:
5'-GCTGCTTTRAGACCTTATCGAAA-3'   (SEQ ID NO: 1)

(P2) antisense:
5'-ATACTGCAGCYCGATGGCCAG-3'     (SEQ ID NO: 2)
```

First strand cDNA was synthesized from total RNA using either random hexamers, 0.5 μg oligo(dt), or the antisense primer. 0.5 unit Inhibit-ACE™ was added. Synthesis of first strand cDNA was performed in 20 μl total volume with 0.5 unit Inhibit-ACE™first strand buffer, 10 mM dithiothreitol, 0.5 mM each of dATP, dCTP, dGTP, dTTP, and 200 units MMLV reverse transcriptase (at 42° C. for 1 h. The addition of the reverse transcriptase was omitted in control samples to check for DNA contamination of the RNA preparations. Sheep lung tissues from disease jaagsiekte lungs served as positive control. PCR cycles employed were 94° C. for 1 minute and 35 cycles of 94° C. for 45 sec, 57° C. for 1 min and 72° C. for 1 min, with a final extension of 72° C. for 2 min in a Perkin-Elmer Gen Amp 2400 thermal cycler. PCR products were sequenced by ligating in a TA cloning vector (Invitrogen) and analyzed on an Applied Biosystems Model 373A automated sequencer.

Surprisingly, the RT-PCR performed on representative cases of human BAC which were JSRV immunopositive revealed the expression of JSRV gag transcripts which were 95–100% identical to both the endogenous and exogenous gag transcripts (distinguished by a ScaI site) expressed in sheep jaagsiekte. The human cases which were analyzed differed slightly from one another and from sheep jaagsiekte tissues. However when the analyses were repeated on separate days and from starting from frozen tissues, 100% agreement in sequences were obtained from the same tissue source. Hence PCR contamination could be completely excluded. The majority of the human cases lacked the presence of the ScaI site; one case however had the ScaI site intact (FIG. 4A). The feline BAC line also exhibited expression of JSRV gag transcripts containing the ScaI site which were 91.7% identical to the sheep JSRV (FIG. 3A; FIG. 4A).

A summary of the information provided in FIG. 4A is provided in the Table below.

| | COMPARISON TO EXOGENOUS | | | COMPARISON TO ENDOGENOUS | |
|---|---|---|---|---|---|
| | Mismatches | Homology | Sca I Site | Mismatches | Homology |
| BAC 1: | 6 | 97.4% | Absent | 10 | 95.6% |
| BAC 2: | 4 | 98.3% | Absent | 6 | 97.4% |
| BAC 3: | 6 | 97.4% | Absent | 8 | 96.5% |
| BAC 4: | 9 | 96.1% | Absent | 10 | 95.6% |
| BAC 5: | 0 | 100.0% | Present | 11 | 95.2% |
| F BAC: | 19 | 91.7% | Present | 24 | 89.5% |

In many of these human cases and in the feline line, none of the disparities in base divergence resulted in a change in amino acid composition (FIG. 4B). However one human BAC case had a valine substituted for a glycine at bp position 1625–1627 and a valine substituted for aspartic add at bp position 1640–1642; another human BAC had only the valine substituted for aspartic add at bp position 1640–1642; still a third human BAC had a valine substituted for alanine at bp position 1598–1600 and a valine substituted for aspartic acid at bp position 1649–1651. The ScaI site changed the amino acid at site 1724–1726 from glutamine to glutatnic acid (FIG. 4B).

What is claimed is:

1. A feline bronchioloalveolar carcinoma designated SPARKY-X and having ATCC patent deposit designation PTA-2920.

2. A feline bronchioloalveolar cell line designated SPARICY and having ATCC patent deposit designation PTA-2919.

3. A non-human animal model for bronchioloalveolar carcinoma comprising an immunocornpromnised mouse host inoculated with a feline bronchioloalveolar carcinoma xenograft designated SPARKY-X and havina ATCC patent deposit designation PTA-2920.

4. The animal model according to claim 3, wherein the immunocompromised mouse host is a nude mouse.

5. An assay for assessing the effect of a treatment for bronchioloalveolar carcinoma, comprising:

(a) administering a therapeutic agent to an immune deficient mouse bearing a feline bronchioloalveolar carcinoma xenograft generated by implanting SPARKY-X tissue or a cell suspension thereof in the immune deficient mouse, wherein said tissue having ATCC patent deposit No. PTA-2920; and (a) determining the effect of the agent on the growth of the xenograft in said mouse.

6. The assay according to claim 5, wherein the immune deficient mouse is a nude mouse.

7. A method of identifying a mRNA transcript whose expression is modulated in bronchioloalveolar carcinoma comprising the steps of:

(a) providing a feline bronchioloalveolar carcinoma xenograft designated SPARKY-X and having ATCC patent deposit designation PTA-2920 such that the xenograft grows within an immunocompromised mouse host in a lepidic bronchioloalveolar carcinoma growth pattern;

(b) determining the level of expression of at least one mRNA transcript in the feline bronchioloalveolar xenograft; and (c) comparing the level expression of the mRNA transcript in the feline bronchioloalveolar xenograft to the level of expression of the mRNA transcript in a feline bronchioloalveolar cell isolated from a feline that does not suffer from bronchioloalveolar carcinoma.

8. The method according to claim 7, wherein the level of expression of the mRNA of the bronchioloalveolar carcinoma xenograft is determined by Northern Blotting or polymerase chain reaction.

9. A method of identifying a mRNA transcript whose expression is modulated in bronchioloalveolar carcinoma comprising the steps of:

(a) determining the level of expression of at least one mRNA transcript in the feline lung cancer cell line designated SPARKY as described in ATCC patent deposit No. PTA-2919; and (b) comparing the level expression of the mRNA transcript in the feline lung cancer cell line to the level of expression of the mRNA transcript in a feline bronchioloalveolar cell isolated from a feline that does not suffer from bronchioloalveolar carcinoma.

* * * * *

UNITED STATES PATENT AND TRADEMARK OFFICE

CERTIFICATE OF CORRECTION

PATENT NO. : 7,220,891 B2
APPLICATION NO. : 10/477501
DATED : May 22, 2007
INVENTOR(S) : Barsky et al.

It is certified that error appears in the above-identified patent and that said Letters Patent is hereby corrected as shown below:

In the Claims:

Column 39:

Claim 2, lines 17 and 18, please delete “SPARICY” and insert --SPARKY--.

Signed and Sealed this

Twenty-sixth Day of October, 2010

David J. Kappos
*Director of the United States Patent and Trademark Office*